United States Patent
Campell et al.

[11] Patent Number: 6,059,724
[45] Date of Patent: May 9, 2000

[54] SYSTEM FOR PREDICTING FUTURE HEALTH

[75] Inventors: T. Colin Campell, Ithaca, N.Y.; Ronald W. Helms, Chapel Hill; Lisa Tomasko, Durham, both of N.C.

[73] Assignee: BioSignal, Inc., Chapel Hill, N.C.

[21] Appl. No.: 08/800,314

[22] Filed: Feb. 14, 1997

[51] Int. Cl.$^7$ .................................................. A61B 5/00
[52] U.S. Cl. ................................ 600/300; 128/923
[58] Field of Search ................................ 600/300, 301; 128/920, 923–925

[56] References Cited

U.S. PATENT DOCUMENTS

| | | |
|---|---|---|
| 4,733,354 | 3/1988 | Potter et al. . |
| 4,975,840 | 12/1990 | De Tore et al. . |
| 5,083,571 | 1/1992 | Prichep . |
| 5,130,936 | 7/1992 | Sheppard et al. . |
| 5,224,035 | 6/1993 | Yamashita et al. . |
| 5,265,244 | 11/1993 | Ghosh et al. . |
| 5,343,390 | 8/1994 | Doi et al. . |
| 5,359,700 | 10/1994 | Seligson . |
| 5,687,716 | 11/1997 | Kaufmann et al. ..................... 600/300 |
| 5,692,501 | 12/1997 | Minturn .................................. 600/301 |

FOREIGN PATENT DOCUMENTS

| | | |
|---|---|---|
| WO 93/12255 | 6/1993 | European Pat. Off. . |
| WO 96/12187 | 4/1996 | European Pat. Off. . |

OTHER PUBLICATIONS

W.B. Kannel, E.D. Eaker, Psychosocial and other features of coronary heart disease: insights from the Framingham Study, Am. Heart Journ. 112: 1066–1073, 1986.

D.J.P. Barker, Fetal origins of coronary heart disease, Brit. Med. Journ., 311: 171–174, 1995.

C.H.D. Fall et al., Relation of infant feeding to adult serum cholesterol concentration and death from ischaemic heart disease, Brit. Med. Journ., 304: 801–801, 1992.

Faris, R.A. and Campbell, T.C., Permanently altered chemical carcinogen metabolism as related to the neonatal environment, Science 211: 719–721, 1981.

(List continued on next page.)

*Primary Examiner*—Eric F. Winakur
*Attorney, Agent, or Firm*—Kenyon & Kenyon

[57] ABSTRACT

A computer-based system is disclosed for predicting future health of individuals comprising:

(a) a computer comprising a processor containing a database of longitudinally-acquired biomarker values from individual members of a test population, subpopulation D of aid members being identified as having acquired a specified biological condition within a specified time period or age interval and a subpopulation $\bar{D}$ being identified as not having acquired the specified biological condition within the specified time period or age interval; and (b) a computer program that includes steps for:
  (1) selecting from said biomarkers a subset of biomarkers for discriminating between members belonging to the subpopulations D and $\bar{D}$, wherein the subset of biomarkers is selected based on distributions of the biomarker values of the individual members of the test population; and
  (2) using the distributions of the selected biomarkers to develop a statistical procedure that is capable of being used for:
    (i) classifying members of the test population as belonging within a subpopulation PD having a prescribed high probability of acquiring the specified biological condition within the specified time period or age interval or as belonging within a subpopulation $\overline{PD}$ having a prescribed low probability of acquiring the specified biological condition within the specified time period or age interval; or
    (ii) estimating quantitatively, for each member of the test population, the probability of acquiring the specified biological condition within the specified time period or age interval.

30 Claims, 2 Drawing Sheets

OTHER PUBLICATIONS

Rodriguez et al., "A Computer Program for Application of Epidemiological Analysis," Eur. J. Epidemiol. 1993, 9 (11) 1–4.

J.W. Furlong et al., "Neural Network Analysis of Serial Cardiac Enzyme Data: A Clinical Application of Artificial Machine Intelligence", Amer. J. Clinical Pathology, Vol. 96, No. 1, Jul., 1991, pp. 134–141.

M.L. Astion et al., "Application of Neural Networks to the Interpretation of Laboratory Data in Cancer Diagnosis", Clinical Chemistry, vol. 38, No. 1, 1992, pp. 34–38.

P. Wilding et al., "Application of Backpropagation Neural Networks to Diagnosis of Breast and Ovarian Cancer", Cancer Letters, vol. 77, 1994, pp. 145–153.

G. Reibnegger et al., "Neural Networks as a Tool for Utilizing Laboratory Information: Comparison with Linear Discriminant Analysis and with Classification and Regression Trees", Proceedings of the National Academy of Sciences, vol. 88, Dec., 1991, pp. 114126–11430.

Encyclopedia of Statistical Sciences, edited by Samuel Kotz, Normal L. Johnson, and Campbell B. Read, published by John Wiley & Sons, 1985, Correlation Analysis (vol. 2, pp. 193–204).

Encyclopedia of Statistical Sciences, edited by Samuel Kotz, Normal L. Johnson, and Campbell B. Read, published by John Wiley & Sons, 1985, Logistic Regression Analysis (vol. 5, pp. 128–133).

Encyclopedia of Statistical Sciences, edited by Samuel Kotz, Normal L. Johnson, and Campbell B. Read, published by John Wiley & Sons, 1985, Mixed Model Analysis (vol. 3, pp. 137–141, article "Fixed–, Random–, and Mixed–Effect Models").

Encyclopedia of Statistical Sciences, edited by Samuel Kotz, Normal L. Johnson, and Campbell B. Read, published by John Wiley & Sons, 1985, Discriminant Analysis (vol. 2, pp. 389–397).

Tangen, Catherine M., and Helms, Ronald W., (1996), "A case study of the analysis of multivariate longitudinal data using mixed (random effects) models," (Abstract) presented at the 1996 Spring Meeting of the International Biometric Society, Eastern North American Region, Richmond, Virginia, Mar., 1996.

Grady, J. J. and Helms, R. W. (1995), "Model Selection Techniques for the Covariance Matrix for Incomplete Longitudinal Data." Statistics in Medicine, 14, 1397–1416.

K. M. Anderson, P.W.F. Wilson, P.M. Odell and W.B. Kannel, "An Updated Coronary Risk Profile", AHA Medical/Scientific Statment 356, vol. 83, No. 1, Jan., 1991.

SYSTEM FOR PREDICTING FUTURE HEALTH

FIELD OF INVENTION

A computer-based system and method are disclosed for predicting the future health of an individual. More particularly, the present invention predicts the future health of an individual by obtaining longitudinal data for a large number of biomarkers from a large human test population, statistically selecting predictive biomarkers, and determining and assessing an appropriate multivariate evaluation function based upon the selected biomarkers.

BACKGROUND OF THE INVENTION

It would be desirable if the onset of future health problems could be predicted for an individual with sufficient reliability far enough into the future so that the chances could be increased for preventing future health problems for that individual rather than waiting for actual onset of a disease and then treating the symptoms. At present, the overwhelming fraction of medical research funding is directed toward improving methods of diagnosis and treatment of disease rather than toward discovering preventive measures that could be directed toward reducing the risk of disease long before any of the typically observed symptoms of the disease are evident. Although the emphasis on treatment of diseases may have led to enormous advances in the medical sciences in terms of the large number and great sophistication of the techniques and methods developed for diagnosing existing diseases as well as for treating the diseases after diagnosis, such advances continue to lead to ever-increasing costs for treatment. Such costs can have staggering financial consequences for individuals as well as for the entire society. Such staggering costs have led to increasing public pressure to find ways of reducing medical costs.

Thus, in addition to the benefit to be gained by an individual who could be informed of the high risk of the onset of disease far enough in advance so that effective preventive steps could be taken, substantial reductions in overall medical costs might be realized by entire communities and/or countries.

Until now, two of the problems inherent in attempting to assess or predict an individual's future health are: (a) such predictions are imprecise because they are based on data obtained from relatively small study samples, consisting of a few hundred or even a few thousand subjects, and (b) the predictions require extrapolation to individual persons from the mean (and other parameters) of that sample. Such extrapolations are highly problematic with respect to reliably estimating the risk of a specific individual, even within a group at high risk for a specific disease. This is true, in part, because the statistical procedures that are typically used are designed to make inferences about population means, not about individual members of the population.

To obtain quantitative predictions, an "individual's future health" must be designated as the occurrence of a specific event within a specified timeframe. Two examples are: (a) occurrence of a myocardial infarction within the succeeding five years, (b) the individual's death within the next year. Predictions of such events are necessarily probabilistic in nature.

Two types of probability are important in this context. The a priori probability of an event is the probability of the event, before the fact of the event's occurrence or non-occurrence. The post hoc probability of an event is the probability of the event after the event is realized, i.e., after the event's occurrence or non-occurrence. Clearly the post hoc probability of an event is 1 if the event occurred and 0 if the event did not occur. The distinction between the a priori probability and post hoc probability is worthy of note.

The a priori probability of an event occurring in the subsequent year, or other time interval, can be important information. Knowledge of the probability of an event can modify behavior or, put another way, the actions one takes (behavior) can depend on the a priori probability of an event. This principle is made self evident by considering two extreme cases. One would almost surely exhibit different behaviors (take different actions) under the two scenarios: one is informed that one's probability of death in the coming year is (a) 0.9999, or (b) 0.0001.

The a priori probability of an event depends upon the information available at the time the probability is evaluated. To illustrate the point, consider the following hypothetical "game."

A living, person will be selected at random from all U.S. residents and followed for a period of one year. At the end of the year the person's vital status (alive or dead) will be ascertained. The "event" is "the person died during the year." At the end of the year the event either occurred (person died) or did not occur (person survived) with post hoc probabilities of 1 and 0, respectively. Before the person is selected, the U.S. mortality statistics can be used to estimate the a priori probability that the person will die in the year. This probability is computed as $p=d/N$, where N is the total number of persons in the at risk group (here, all the persons in the U.S. population who were alive at the beginning of the year) and d is the total number of deaths among the at risk group. For example, the data from calendar year 1993 are (approximately), $d=2,268,000$, $N=257,932,000$, and the a priori probability of the event is approximately $p=0.0088$. [Data from *Microsoft Bookshelf* 1995 *Almanac*, article entitled, "Vital Statistics, Annual Report for the Year 1993 (Provisional Statistics), Deaths." and *Vital Statistics of the United States*, published by the National Center for Health Statistics.] In this game, the a priori probability of the event is based upon very little information, simply that the person would be a member of the at risk group, consisting of all persons who would be alive and a U.S. resident at the time of selection.

Additional information about the at risk group, from which the subject is selected at random, implies additional information about the subject and modification of the a priori probability of the event. For example, continuing the "game" above, based on 1993 data:

If the at risk group were the group of U.S. males, i.e., if the subject is known, prior to selection, to be a male, the a priori probability of the event is approximately $p=0.0093$, which is about 6% higher than the case where gender is unknown or unspecified.

If the at risk group were the group of U.S. males aged 75–84, i.e., if the subject is known, prior to selection, to be a male in the age interval 75–84, the a priori probability of the event is approximately $p=0.0772$, or about 8.3 times as high as for males where age is unknown or unspecified.

These examples illustrate the general principle that the a priori probability of an event depends upon the information available at the time the probability is evaluated. The most accurate estimate of an a priori probability is typically the one based on all of the available information.

A very accurate estimate of an a priori probability does not guarantee a specific outcome; that is, the a priori probability for a specific individual may not be very close to the post hoc probability. Consider the extreme case cited above, where the a priori probability of death of a specific individual in the succeeding year is 0.0001. Although survival is highly probable, it is not guaranteed: of all individuals in this "game," approximately 9,999 of each 10,000 will survive the year and have a post hoc probability of 0 (which is close to the a priori probability, 0.0001) and approximately 1 of each 10,000 will die and have a post hoc probability of 1, which is very different from the a priori probability. To further elucidate this principle, consider a fair coin toss in which the a priori probability of "heads" is exactly 0.5. The post hoc probability of "heads" is either 0 or 1, neither of which is very close to 0.5. Thus, the a priori probability for one individual should not be considered an approximation of the post hoc probability for that individual. However, if a very large number of individuals "play the game," the mean of the post hoc probabilities, which is also the proportion of individuals for whom the event occurs, will be very close to the a priori probability.

In some cases a person can change an a priori probability by "moving" to a group with a different a priori probability. For example, epidemiologists have shown that a U.S. resident, middle-aged male with a high total cholesterol level, including a high low-density lipoprotein level, has a higher a priori probability of death from myocardial infarction in the succeeding five years than a comparable person with a much lower cholesterol level. Clinical trial research has shown that if the high-cholesterol person can reduce his cholesterol level substantially, i.e., "move" to a much lower cholesterol "group," he substantially reduces his a priori probability of death from myocardial infarction in the succeeding five years.

In succeeding paragraphs and sections the word risk will be used in place of the phrase "a priori probability of a specified event within a specified timeframe." This corresponds to the statistical definition of risk as expected loss, where the loss function takes value 1 if the event occurs and 0 if the event does not occur.

The foregoing comments illustrate the principle that differing levels of information lead to differing a priori probabilities. The risk for a person about whom much is known (i.e., a member of a small subpopulation with many known characteristics) may be very different from the risk for a large subpopulation with few known characteristics. However, there is yet another problem confounding the ability of traditional scientific research studies on populations to ascertain risk of disease for individuals. This problem results from a commonly over-simplified understanding of the causation of disease, particularly the causation of chronic degenerative diseases such as cancers, cardiovascular diseases, diabetes, etc. That is, there is a tendency to believe, for a variety of reasons, that such diseases can either be controlled or be clinically indicated by single constituents or by prescribing a single pharmaceutical compound. For example, it has been suggested that breast cancer can be controlled by a modest reduction of fat intake, that colon cancer can be controlled by adding specific dietary fiber components, that heart disease is clinically indicated by elevated blood cholesterol, and that stomach cancer can be clinically indicated by low blood levels of vitamin C. These over-simplified views too often prove to be inadequate for identifying causation, particularly for an individual person. There are too many confounding variables to be taken into consideration, to say nothing of the great difficulties of extrapolating population data to individuals within the population. Testing and investigating single constituents, among a milieu of thousands if not millions of possible constituent causes, is fraught with great uncertainty, especially when attempting to extrapolate these data to the estimation of disease risks for individuals.

These dual difficulties, (a) of extrapolating data for experimental populations of individuals to a randomly selected individual and (b), of relying on single indicators or causes of disease occurrence, seriously compromise estimation of future disease risk for a randomly selected individual. If an individual's risk for a specific disease could be determined more reliably, it then would be possible to provide information to this individual who could then make more informed decisions on his or her personal behavior. In essence, much more reliable methods of predicting future health could become an unusually powerful means for individuals to internalize their own health situation and, thus, to take more effective control of their own well being.

Moreover, for those individuals identified as being at high risk for a particular disease because they may fall within several categories, wherein each individual category is highly correlated with a specific disease, such as heart disease, the currently available methodology typically does not allow one to quantitatively predict when the disease will strike or become fatal for a specific individual with a sufficient reliability or level of confidence to motivate that individual, in general, to take effective steps far enough in advance to significantly reduce that risk. It would, therefore, be desirable to have an effective general purpose tool that would not only reliably predict onset of a specific health problem within a specified time period, but such a tool would also be useful for monitoring the preventive measures that are taken based on such predictions.

ADVANTAGES AND SUMMARY OF THE INVENTION

The present invention is directed to providing a tool for assessing an individual subject's risk of future disease so that greater effort can be made by that individual to the prevention rather than the treatment of disease.

More specifically, the present invention is directed at providing a general tool for quantitatively predicting the risk, for a selected individual, of a wide range of diseases with substantially higher probabilities further into the future and with greater reliability than is now possible.

In particular, the present invention is directed toward providing a computer-based method and apparatus that provides an on-going system for assessing future health risks for a specific individual, and for monitoring the preventive measures taken so as to reduce future health risks for that specific individual.

The present invention identifies sets of selected biomarkers containing information on the probability that an individual will acquire a specified biological condition within a specified time period or age interval and uses cross-sectional and/or longitudinal values of those biomarkers to estimate the individual's risk.

Still more particularly, the present invention is directed to a computer-based system for predicting future health of individuals comprising:

(a) a computer comprising a processor containing a database of longitudinally-acquired biomarker values from individual members of a test population, subpopulation D of said members being identified as having acquired a specified biological condition within a specified time period or age interval and a subpopulation $\overline{D}$ being identified as not having acquired the specified biological condition within the specified time period or age interval; and (b) a computer program that includes steps for:
  (1) selecting from said biomarkers a subset of biomarkers for discriminating between members belonging to the subpopulations D and $\overline{D}$, wherein the subset of biomarkers is selected based on distributions of the biomarker values of the individual members of the test population; and
  (2) using the distributions of the selected biomarkers to develop a statistical procedure that is capable of being used for:
    (i) classifying members of the test population as belonging within a subpopulation PD having a prescribed high probability of acquiring the specified biological condition within the specified time period or age interval or as belonging within a subpopulation $\overline{PD}$ having a prescribed low probability of acquiring the specified biological condition within the specified time period or age interval; or
    (ii) estimating quantitatively, for each member of the test population, the probability of acquiring the specified biological condition within the specified time period or age interval.

The present invention is further directed, inter alia, to a computer-based system for predicting an individual's future health comprising:
(a) a computer comprising a processor containing a plurality of biomarker values from an individual; and
(b) a computer program that includes steps for applying a statistical procedure to said plurality of biomarker values so as:
  (i) to classify said individual as having a prescribed high probability of acquiring a specified biological condition within a specified time period or age interval or as having a prescribed low probability of acquiring the specified biological condition within the specified time period or age interval; or
  (ii) to estimate quantitatively, for said individual the probability of acquiring the specified biological condition within the specified time period or age interval;
wherein said statistical procedure is based on:
  (1) collecting a database of longitudinally-acquired biomarker values from individual members of a test population, subpopulation D of said members being identified as having acquired the specified biological condition within the specified time period or age interval and a subpopulation $\overline{D}$ being identified as not having acquired the specified biological condition within the specified time period or age interval;
  (2) selecting from said biomarkers a subset of biomarkers for discriminating between members belonging to the subpopulations D and $\overline{D}$, wherein the subset of biomarkers is selected based on distributions of the biomarker values of the individual members of the test population; and
  (3) using the distributions of the selected biomarkers to develop said statistical procedure.

Further objectives and advantages of the present invention will be apparent to those skilled in the art from the detailed description of the disclosed invention.

DETAILED DESCRIPTION OF THE PREFERRED EMBODIMENTS

Figure 1:
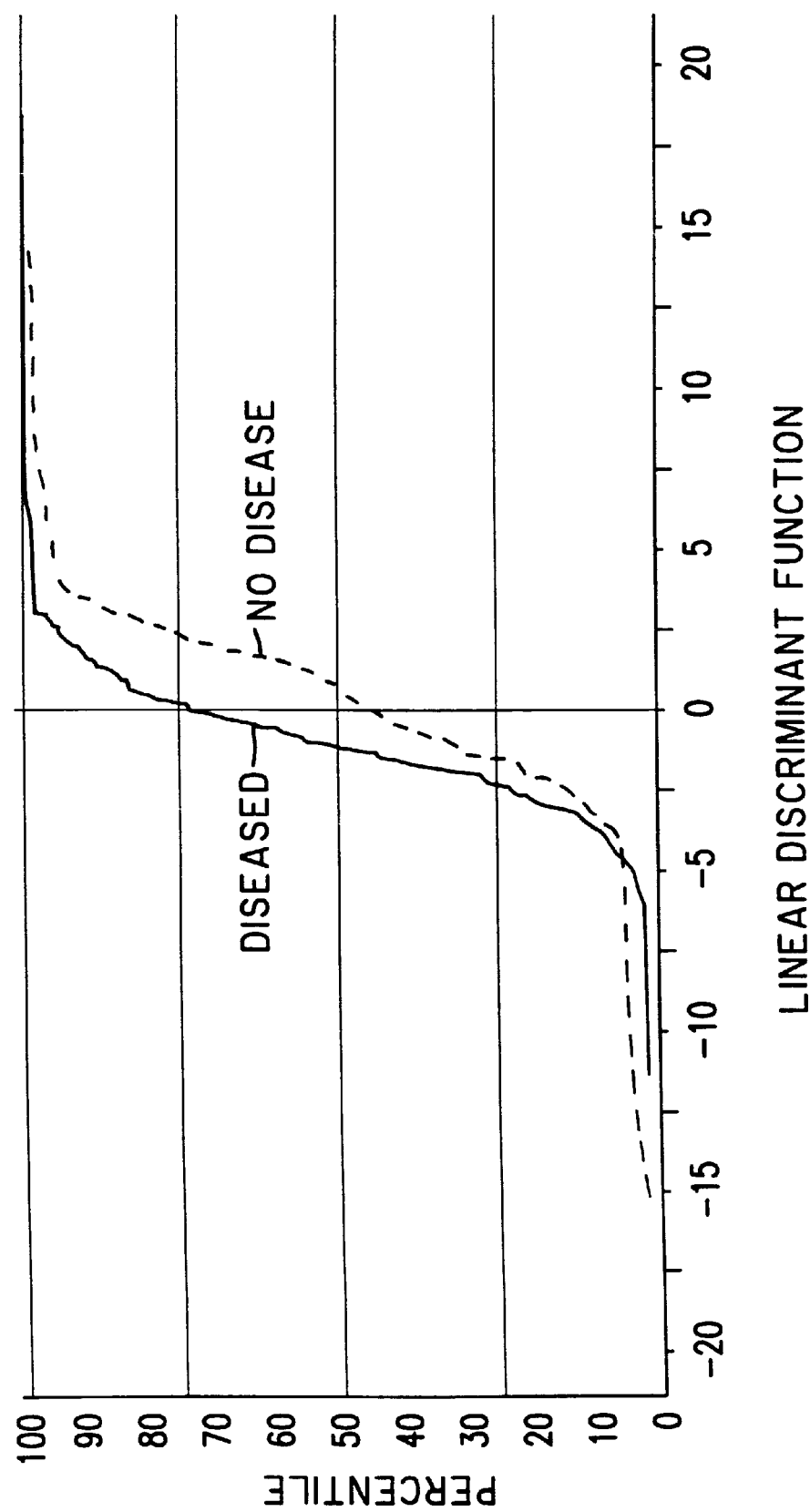
FIG. 1 shows the empirical distribution functions ("EDF") of the linear discriminant function values, based on estimation, for Group D (solid line) and Group $\overline{D}$ (dashed line) of the Example.

The present invention will now be described in detail for specific preferred embodiments of the invention, it being understood that these embodiments are intended as illustrative examples and the invention is not to be limited thereto.

The present invention is based on the theory that an individual's health is, in general, influenced by a complex interaction of a wide range of physiological and biochemical parameters relating to the nutritional, toxicological, genetic, hormonal, viral, infective, anthropometric, lifestyle and any other states potentially describing the aberrant physiological and putative pathological states of that individual. Based on this theory, the present invention is directed towards providing a practical system for predicting future health using multivariate statistical analysis techniques that are capable of providing quantitative predictions of one's future health based on statistically comparing an individual's set of biomarker values with a longitudinally-obtained database of sets of a large number of individual biomarker values for a large test population. The term "biomarker" is used herein to refer to any biological indicator that may affect or be related to diagnosing or predicting an individual's health. The term "longitudinal" is used herein to refer to the fact that the biomarker values are to be periodically obtained over a period of time, in particular, on at least two measurement occasions.

The frequency and duration of longitudinal assessments may vary. For example, some biomarkers may be assessed annually, for periods ranging from as short as 2 years to a period as long as a total lifetime. Under some circumstances, such as evaluation of newborn children, biomarkers could be assessed more frequently as, for example, daily, weekly, or monthly. Longitudinal assessment occasions may be "irregularly timed," i.e., occur at unequal time intervals. The set of longitudinal assessments for an individual may be "complete," meaning that data from all scheduled assessments and all scheduled biomarkers are actually obtained and available, or "incomplete," meaning that the data are not complete in some manner. An individual's biomarkers may be assessed either cross-sectionally, i.e., at one point in time, or longitudinally. The present invention is capable of performing the required statistical analyses of data from individuals that have any or all of the characteristics noted above, i.e., cross-sectional or longitudinal, regularly or irregularly timed, complete or incomplete.

The subject system for assessing future health provides a quantitative estimate of the probability of an individual acquiring a specified biological condition within a specified period of time. The quantitative probability estimate is calculated using the sequence of statistical analyses of the present invention. The subject system may typically be used to provide quantitative predictions of future biological conditions for one, two, three, five, or, ultimately, even 15–20 or more years into the future. Although the subject system may typically be used long before symptoms of a particular disease are usually observed or detected, the subject system may also be used for predicting future health over relatively short time periods of only a few months or weeks, or even shorter time periods, as well.

While there is no upper limit to the number of members that may included in the test population, which might eventually include several million test members, a representative test population may include far smaller numbers initially. The test population may be selected from a much larger general population using appropriate statistical sampling techniques for improving the reliability of the data collected.

In a representative embodiment, the present invention is directed to a computer-based system that uses a series of statistical analysis steps for creating mathematical-statistical functions that can be used to estimate an individual's risk of acquiring a specified biological condition within a specified time period or age interval and to identify individuals that are at highest risk. Prior to Phase I of the subject method, the available subjects may be randomly assigned to a Training Sample or an Evaluation Sample; Phases I–III operate on data from the Training Sample and Phase IV operates on data from the Evaluation Sample. Phase I is a Screening Phase that uses correlation, logistic regression, mixed model, and other analyses to select a large subset of biomarkers that have potentially useful information for risk estimation.

Phase II is a Parameter Estimation Phase that uses mixed linear models to estimate expected value vector and structured covariance matrix parameters of the Candidate Biomarkers, even in the presence of incomplete data and/or irregularly timed longitudinal data. Phase III is a Biomarker Selection and Risk Assessment Phase that uses discriminant analysis methodology and logistic regression to select informative biomarkers (including, where relevant, longitudinal assessments), to estimate discriminant function coefficients, and to use an inverse cumulative distribution function and logistic regression to estimate each individual's risk. Phase IV is an Evaluation Phase that uses the Evaluation Sample to produce unbiased estimates to the misclassification rates of the discriminant procedure.

Although the individual steps of the statistical procedures noted in the previous paragraph are described in the statistical literature, it is believed that these individual steps have never been combined in a single overall procedure as disclosed herein. In particular, classical versions of the following procedures are described for example, in the *Encyclopedia of Statistical Sciences*, edited by Samuel Kotz, Normal L. Johnson, and Campbell B. Read, published by John Wiley & Sons, 1985 and in additional literature cited therein: (a) correlation analysis (Volume 2, pp. 193–204), (b) logistic regression analysis (Volume 5, pp. 128–133), (c) mixed model analysis (Volume 3, pp. 137–141, article "Fixed-, Random-, and Mixed-Effect Models"), (d) discriminant analysis (Volume 2, pp. 389–397). The present invention can utilize classical versions of these procedures or such enhancements to and newer versions of these procedures as may be developed and published from time to time.

Correlation analysis is a term for statistical methods used for estimating the strength of the linear relationship between two or more variables. Correlation, as used here, can include a variety of types of correlation, including but not limited to: Pearson product-moment correlations, Spearman's $\rho$, Kendall's $\tau$, the Fisher-Yates $r_F$, and others.

Logistic regression is a term for statistical methods, including log-linear models, used for the analysis of a relationship between an observed dependent variable (that may be a proportion, or a rate) and a set of explanatory variables. The applications of the logistic regression (or other log-linear models) used herein are primarily for the analysis in which the dependent variable is a binary outcome representing an individual's membership in one of two complementary (non-overlapping) groups of subjects: a group that will acquire a specified disease or condition (sometimes referred to herein as a "specified biological condition") within a specified period of time or age interval, and a group that will not acquire the specified disease or condition within a specified period of time or age interval. In this context the explanatory variables are typically biomarkers or functions of biomarkers.

Mixed model analysis is a term for statistical methods used for the analysis of expected-value relationships between correlated dependent variables (multivariate measurements or observations, longitudinal measurements/observations of one variable, and/or longitudinal multivariate measurements/observations) and "independent variables" that can include covariates, such as age, classification variables (representing group membership) and also used for analysis of structures and parameters representing covariances among correlated measurements/observations. The term "mixed models" includes fixed-effects models, random-effects models, and mixed-effects models. Mixed models may have linear or nonlinear structures in the expected-value model and/or in the covariance model. A mixed model analysis typically includes estimation of expected value parameters (often denoted $\beta$) and covariance matrix parameters (often of the form $\Sigma=Z\Delta Z'+V$, where $\Delta$ and V are matrices of unknown parameters). A mixed model analysis may also include predictors of random subject effects (often denoted $d_k$ for the k-th subject) and so-called "best linear unbiased predictors" (or "BLUPs") for individual subjects. A mixed model analysis typically includes procedures for testing hypotheses about expected value parameters and/or covariance parameters and for constructing confidence regions for parameters.

In particular, discriminant analysis methodology relates to statistical analysis methods and techniques for developing discriminant functions that may be used for assigning a multivariate observation (e.g., a vector of biomarker values from one subject) to one of two complementary (non-overlapping) groups of subjects (e.g., a group that will acquire a specified disease or condition within a specified period of time or age interval, and the group that will not acquire the specified disease or condition within a specified period of time or age interval), on the basis of its value. A discriminant function, furthermore, may refer to a function that is used as the basis for calculating an estimate of the probability that a given observation belongs in a given group. For the present invention, the observations of interest typically comprise a plurality of biomarker values that are obtained from each member of a large test population or from an individual test subject. The discriminant functions of the present invention are developed using distributions of these biomarker values for each biomarker determined to be of interest. Such distributions plot the total number of individual members of the test population having each biomarker value vs. the biomarker value itself. Thus, the present invention empolys a statistical procedure that uses distributions based on the individual biomarker values that are obtained for each biomarker from individual members from the test population, as distinct, for example, from using mean biomarker values that are obtained from different test populations for the different biomarkers.

The term "discriminant function" is intended to mean any one of several different types of functions or procedures for classifying an observation (scalar or vector) into two or more groups, including, but not limited to, linear discriminant functions, quadratic discriminant functions, nonlinear discriminant functions, and various types of so-called optimal discriminant procedures.

The computer-based system of the present invention includes a computer comprised of a processor that is capable of running a computer program or set of computer programs (hereinafter refined to simply as "the computer program") comprising the steps for performing the required computations and data processing in the various steps and phases of the present invention. The processor may be a microprocessor, a personal computer, a mainframe computer, or in general, any digital computer that is capable of running computer programs that can perform the required computations and data processing. The processor typically includes a central processing unit, a random access memory (RAM), read-only memory (ROM), one or more buses or channels for transfer of data among its various components, one or more display devices (such as a "monitor"), one or more input-output devices (such as floppy disk drives, fixed disk drives, printers, etc.), and adapters for controlling input-output devices and/or display devices and/or connecting such devices to the buses/channels. A particular processor may include all of these components or only a subset of these components.

The computer program may be stored in ROM or on a disk or set of disks, or in any other tangible medium that may be used for storing and distributing computer programs.

The computer program is capable of performing the computations for the various phases and steps of the analysis on cross-sectional and/or longitudinal multivariate biomarker data.

The biomarker data are preferably collected from a test population that is sufficiently large so that the total number of members acquiring a specified biological condition of interest within a two to three year period is large enough for discriminant analysis methodology to be meaningfully employed for that specified biological condition. Since one of the features of the present invention is directed toward providing a means for using the same database to make predictions relating to acquiring any of the major diseases and/or dying from any of the major underlying causes of death within as few as one to two years, the test population is preferably large enough to be useful for applying the subject system to any one of the more common diseases and underlying causes of death that account in the aggregate for at least about 60%, and more preferably, at least about 75%, of all deaths of interest, wherein the deaths of interest are herein defined as those of a pathological nature, as distinct from those caused by accident, homicide or suicide.

For example, using data from Center for Disease Control and Prevention (Monthly Vital Statistics Report, Supplement, Vol. 44, No. 7, Feb 26, 1996), it can be shown that more than 75% of all pathologically derived deaths can be accounted for by the following underlying causes of death, malignant neoplasms (ICD 140–208) having a crude death rate, that is, as distinguished from an age-adjusted death rate, of 205.6/100,000; major cardiovascular diseases (ICD 390–448), 367.8/100,000; chronic obstructive pulmonary diseases, (ICD 490–496), 39.2/100,000; and diabetes mellitus (ICD 250), 20.9/100,000; as compared with a total crude death rate of about 880/100,000 for pathologically derived deaths. These diseases are the ones which, in fact, have been shown to exhibit major dietary and lifestyle effects, to be responsive to altered dietary and lifestyle conditions, and to be indicated by a variety of definable and measurable biomarkers.

As one of the unique features of the present invention, the subject computer-based system and apparatus may be used to determine the risk of a specified individual acquiring any one of these major diseases based on comparing that individual's profile of biomarker values with the biomarker values obtained from members of a large test population. Since it is known that these major diseases share many common factors that may be reflected in the biomarker values, the subject computer-based system may be used to concurrently assess the risk of acquiring any of these major diseases. For example, it is known that total serum cholesterol is a biomarker that is related to many of these diseases. By monitoring each profile of biomarker values that is a significant predictor, in combination with other significant biomarker predictors, of a specific disease or underlying cause of death and using the present invention to compare that profile with the test populations, an individual subject may be informed, with specified quantitative reliability, which disease poses the greatest risk for that specific individual.

A particular feature of the present invention is that those individuals who are at greatest risk of acquiring a specified disease may be provided with a quantitative probability of acquiring that disease within a specified time period or age interval in the future well before any of the typical symptoms of that disease are manifest. Armed with that information, for the many diseases known to be responsive to altered dietary and lifestyle conditions, that individual may then make those behavioral changes that can reduce the risk of the disease identified.

Furthermore, as more and more data are acquired for larger and larger numbers of subjects over longer and longer periods of time, more and more refined divisions of each of the major diseases and causes of deaths as well as of the less common diseases and underlying causes of death can be defined and included in the methodology of the present invention. For example, a breakdown can be made in terms of the different types of cancer, e.g., liver cancer, lung cancer, stomach cancer, prostate cancer, etc. The present computer-based system, thus, provides a means for including ever larger fractions of the population, so as to predict the quantitative risk of each individual acquiring, or not acquiring, a specified pathologically derived disease within a specified time, wherein the diseases are defined with continuously narrower specificity.

The comprehensive set of biomarkers for which biomarker data are collected from the test population preferably includes as many as possible of the diverse biomarkers known or believed to be related to the most common diseases and underlying causes of pathologically derived deaths. In addition, representative clusters of biomarker values from each of the known and generally accepted genetic, physiological and biochemical domains of biological function may be included. Additional biomarkers that are preferably included are, for example, all those that can be measured in biological samples that may be stored for analysis long after the sample is collected.

The biological samples preferably include a blood and a urine sample, but still other biological samples may be included in the samples that are collected. For example, samples of saliva, hair, toenails and fingernails, feces, expired air, etc. may also be collected. Such biological samples are typically obtained from substantially every member of the test population. However, in some situations, specific subsets of biomarkers may be obtained only from specific subsets of the population.

Concurrent with collecting the biological samples, biomarker data relating to nutritional habits and lifestyles are also typically obtained from each member of the test population. Biomarkers relating to nutritional habits and life styles may include, for example, those shown in Table 1. While the nutritional- and life-style-biomarkers listed in Table 1 are intended to be illustrative of the types of biomarkers relating to nutritional habits and life styles, it is to be understood this list is not exhaustive of the nutritional and life style biomarkers that fall within the scope of the present invention. The biomarkers that exhibit significant nutritional determinism, as well as the clinical and infections biomarkers, may also be determined by other factors, such as by nutritional intake. The delineation of categories, (e.g. serum biomarkers, urine biomarkers, questionnaire, etc.), shown in Table 9 is, thus, only an illustrative division of the categories that may be selected to obtain the biomarker values. The nutritional and life style biomarkers that may change over time are preferably collected and recorded for each member of the test population each time a biological sample is taken.

TABLE 1

An illustrative list of biomarkers that may be used in the subject method for predicting future health.

SERUM BIOMARKERS

Total cholesterol*
HDL cholesterol*
LDL cholesterol*
Apolipoprotein b*
Apolipoprotein $A_1$*
Triglycerides*
Lipid peroxide (Malondialdehyde equivalency:TBA)*
α-Carotene (corrected for lipoprotein carrier)*
β-Carotene (corrected for lipoprotein carrier)*
γ-Carotene (corrected for lipoprotein carrier)*
zeta-Carotene (corrected for lipoprotein carrier)*
α-Cryptoxanthin (corrected for lipoprotein carrier)*
β-Cryptoxanthin (corrected for lipoprotein carrier)*
Canthaxanthin (corrected for lipoprotein carrier)*
Lycopene (corrected for lipoprotein carrier)*
Lutein (corrected for lipoprotein carrier)*
anhydro-Lutein (corrected for lipoprotein carrier)*
Neurosporene (corrected for lipoprotein carrier)*
Phytofluene (corrected for lipoprotein carrier)*
Phytoene (corrected for lipoprotein carrier)*
α-Tocopherol (corrected for lipoprotein carrier)*
γ-Tocopherol (corrected for lipoprotein carrier)*
Retinol*
Retinol binding protein*
Ascorbic acid*
Fe*
K*
Mg*
Total phosphorus*
Inorganic phosphorus*
Se*
Zn*
Ferritin*
Total iron binding capacity*
Fasting glucose*
Urea nitrogen*

TABLE 1-continued

An illustrative list of biomarkers that may be used in the subject method for predicting future health.

Uric acid*
Prealbumin*
Albumin*
Total protein*
Bilirubin*
Thyroid stimulating hormone T3*
Thyroid stimulating hormone T4*
Cotinine
Aflatoxin-albumin adducts
Hepatitis B anti-core antibody (HbcAb)
Hepatitis B surface antigen (GhsAg+)
Candida albicans antibodies
Epstein-Barr virus antibodies
Type 2 Herpes Simples antibodies
Human Papiloma virus antibodies
Heliocobacter pylori antibodies
Estradiol (E2) (adjusted for female cycle)*
Sex hormone binding globulin*
Prolactin (adjusted for female cycle)*
Testosterone (adjusted for female cycle for women)*
Hemoglobin*
Myristic acid (14:0)*
Palmitic acid (16:0)*
Stearic acid (18:0)*
Arachidic acid (20:0)*
Behenic acid (22:0)*
Tetracosaenoic acid (24:0)*
Myristicoleic acid (14:1)*
Palmitoleic acid (16:1)*
Oleic acid (18:1n9)*
Gadoleic acid (20:1)*
Erucic acid (22:1n9)*
Tetracosaenoic acid (24:1)*
Linoleic (18:2n6)*
Linoleic acid (18:3n3)*
γ-Gamma linoleic (18:3n6)*
Eicosadienoic acid (20:2n6)*
Di-homo-γ-linolenic acid (20:3n6)*
Arachidonic acid (20:4n6)*
Eicospentaenoic acid (20:5n3)*
Docosatetraenoic acid (22:4n6)*
Docosapentaenoic acid (22:5n3)*
Docosahexaenoic acid (22:6n3)*
Total saturated fatty acids (16:0, 18:0, 20:0, 22:0, 24:0)*
Total monounsaturated fatty acids (14:1, 16:1, 18:1n9, 20:1, 24:1)*
Total n3 polyunsaturated fatty acids (18:3n3, 20:5n3, 22:5n3, 22:6n3)*
Total n6 polyunsaturated fatty acids (18:3n6, 20:2n6, 20:3n6, 20:4n6, 22:4n6)*
Total n3 polyunsaturated/total n6 polyunsaturated fatty acids (18:3n3, 20:5n3, 22:5n3, 22:6n3/18:3n6, 20:2n6, 20:3n6, 20:4n6, 22:4n6)*
Total polyunsaturated fatty acids (18:2n6, 18:3n3, 18:3n6, 20:2n6, 20:3n6, 20:4n6, 20:5n3, 22:4n6, 22:5n3, 22:6n3)*
Total polyunsaturated/saturated fatty acids (18:2n6, 18:3n3, 18:3n6, 20:2n6, 20:3n6, 20:4n6, 20:5n3, 22:4n6, 22:5n3, 22:6n3/16:0, 18:0, 20:0, 22:0, 24:0)*
[About 10–30 genetic markers, depending on diseases being investigated]

URINE BIOMARKERS

Orotidine
Cl*
Mg*
Na*
Creatinine
Volume
$NO_3$
Aflatoxin (AF) $M_1$
AF $N^7$ guanine

TABLE 1-continued

An illustrative list of biomarkers that may be used in the subject method for predicting future health.

AF $P_1$
AF $Q_1$
Aflatoxicol
8-deoxy guanosine
FOOD DERIVED NUTRIENT
INTAKES (FROM QUESTIONNAIRE)

Total protein*
Animal protein*
Plant protein*
Fish protein*
Lipid*
'Soluble' carbohydrate*
Total dietary fiber*
Total calories*
Percentage of caloric intake from lipids*
Cholesterol*
Ca*
P*
Fe*
K*
Mg*
Mn*
Na*
Se*
Zn*
Total tocopherols (corrected for lipid intake)*
Total retinoid*
Total carotenoid*
Thiamine*
Riboflavin*
Niacin*
Vitamin C*
[About 30 different types of foods]*
[About 30 different fatty acids]*
RED BLOOD CELLS RBC glutathione reductase*
RBC catalase*
RBC superoxide dismutase*
ANTHROPOMETRIC PARAMETERS Height*
Weight*

*Indicates biomarkers which exhibit significant nutritional determinism

The biological samples are analyzed to determine the biomarker value for each component in the biological sample for which a biomarker value is desired. It is to be understood that any component that may be found and measured in a biological sample falls within the scope of the present invention. For example, ,genetic biomarkers which may be measured in a blood sample, as well as the biomarkers that can be measured in any other appropriate biological sample, may also be included.

Since another feature of the present invention is that of identifying new sets of biomarkers useful for predicting disease and death, the biomarker sets may include biomarkers not previously known to have statistical significance for predicting a specific disease or specific cause of death. Thus, since the total number of biomarkers that may be used is substantially unlimited in principle, the actual number of biomarkers used may, in general, be limited only by practical economic and methodological considerations.

Since still another feature of the present invention is that of providing a computer-based system for predicting specified biological conditions within a specific time period or age interval in the future, the total number of biomarker values may be limited to only those biomarker values which have statistical significance for predicting a single specified biological condition. Thus, while it is intended that the subject system is typically used as a general purpose tool for predicting and monitoring most, and, eventually, substantially all major types of diseases and underlying causes of death, use of the methodology disclosed herein may also be directed to one disease or cause of death at a time.

After being collected, the biological samples may be analyzed immediately or the samples may be stored for later analysis. Since it is expected that a large number of samples may be collected in a relatively short period of time and under circumstances not conducive to immediate on-site analysis, the samples are preferably stored for later analysis. Because the samples may typically be stored for a substantial period of time, the samples are typically frozen. The samples are to be stored and transported using conditions that preserve the integrity of the samples. Such techniques are described, for example, in Chen, J., Campbell, T. C., Li, J., and Peto, R. Diet, life-style and mortality in China. *A Study of the Characteristics of 65 Chinese Counties*, Oxford, U.K.; Ithaca, N.Y.; Beijing, PRC: Oxford University Press; Cornell University Press; Peoples Medical Publishing House, 1990.

Use of physical specimens such as biological samples are particularly preferred since such samples provide a practical means of providing a rich source of longitudinally-obtained biomarker data that can be collected, stored and analyzed using established, cost-effective techniques. The biological samples are preferably collected for the test population over an extended period of time of at least 5–10 years, and most preferably, for 15–20 years or more, such that the quality of the data generated will continuously provide more and more reliable probability predictions.

Since the reliability of the subject system is ultimately determined by the quality of the biomarker data collected, appropriate measures are to be taken to assure integrity of the data from all aspects. For example, concerning biomarker stability, it is necessary to consider and take appropriate measures to account for the many factors which may influence or cause deterioration of the biomarker values over time.

Furthermore, while the subject disclosure is typically directed toward obtaining biomarker data from physical specimens that are obtained from members of a test population or a test subject, as well as the biomarker data derived from dietary and lifestyle surveys of each test individual, use of biomarker data obtained from any source falls fully within the spirit and scope of the present invention. For example, the subject methodology may further comprise use of medical diagnostic data obtained from electrophysiological measurement techniques such as electroencephalographic (EEG) data, electrocardiographic (ECG) data, radiologic (X-ray) data, magnetic resonance imaging (MRI), etc., either alone or, most preferably, in combination with the longitudinally-obtained biomarker data from biological samples and dietary and lifestyle surveys.

Since the test population is preferably monitored over a period of years, it is to be expected that a mortality rate will be observed for the test population that is representative of the overall general population. For each mortality in the test population, the individual is identified and the underlying cause of death is recorded, preferably using a known coding system, for example, the established *International Statistical Classification of Diseases and Related Health Problems*, (ICD-10), Geneva, World Health Organization, 1992-c1994, 10th revision. Other coding systems may also be used while remaining within the scope and spirit of the present invention.

Using an effective system to identify when a member of the test population acquires a disease or specified biological condition, morbidity data is also collected, in addition to collecting the biomarker and mortality data of the test population.

The database of biomarker values preferably includes information from each individual recording the dates and ages at the times the biomarkers and biomarker samples are collected and recorded, accurate information from the surveillance of the individual recording each incident of disease, medical condition, medical pathology, or death, including diagnosis and date of incident. The database includes values of biomarkers assessed before, during, and after each incident, where feasible.

Since one aspect of the present invention relates to identifying biomarkers not yet known to be statistically significant for predicting future onset of a specified disease or underlying cause of death, as many biomarkers as possible are monitored. In a representative embodiment, about 200 biomarker values are obtained from each member of the test population, although there is substantially no upper limit to the number of biomarkers that may be used to develop the computer-based statistical analysis methodology.

Since the present invention is directed toward providing a practical and reliable system for predicting a specified biological condition within a specified period of time or age interval, a substantially complete set of biomarker values is collected from each member of the test population at least two different times. More preferably, so as to obtain information on trends or changes with time, a full set is collected at least three times and, most preferably, the biomarker values are collected at periodic intervals for as long as practically feasible.

In still another aspect of the subjection invention, which is based on the theory that ratios of a person's individual biomarker values, or changes in the ratios, may be more important for predicting future health than the actual level of any given biomarker value, the discriminant function is typically determined using substantially complete sets of biomarker values. Since it is recognized that for practical reasons totally complete sets of biomarker values cannot reasonably be expected to be obtained from every member of the test population on every testing occasion, the statistical analysis methodology of this invention includes methods that reliably account for incomplete data in a statistically valid manner.

A further object of the present invention is not only to provide a means of quantitatively assessing the risk of future specific diseases, but also to provide a practical tool for defining and identifying those biological conditions wherein one has the lowest risk of all future diseases. The term "specified biological condition" is, therefore, in the context of the present invention, meant to include all ranges of health, from the most robustly healthy to the most severely diseased. The present invention is, thus, directed towards providing a system for monitoring and predicting future health for the most healthy to the least healthy.

Although the results obtained from the test population may be used for predicting the future health of general populations in particular countries, it is not necessary to select the test population from the same general population for which individual future health predictions will be made. Such a limitation is not necessary since it is known that populations of individuals who possess probabilities of disease which are characteristic of their home countries, and who then move to new countries whose populations possess probabilities of different sets of diseases, will acquire those diseases which are characteristic of the countries to which they move. This occurs during a time coincident with and following their acquisition of the diet and lifestyle conditions of the new country. That is, all races and ethnic groups of the world tend to acquire the same general diseases regardless of their inherited characteristics, which may be unique to each race or ethnic group.

One of the specific features of the present invention is that a system is provided for predicting when onset of a future health problem will occur before the problem may typically be diagnosed. The time of future onset of the specific health problem occurring for a specific individual can be predicted with a specified quantitative probability estimate based on applying the subject discriminant analysis methodology to the database collected from the large test population. Furthermore, the present invention provides a system for predicting specific health problems further and further into the future with greater and greater reliability as more and more data are collected for ever larger test populations for longer and longer periods of time.

The biological samples are typically analyzed for each biomarker for which quantitative values are desired. For cost and convenience reasons and because of the large number of samples that may be collected, the samples may be analyzed initially only for those individuals already diagnosed with a disease or who die during the time period over which the samples have been collected, as well as for a randomly selected fraction of the remainder of the test population. For example, if the annual mortality rate for the test population surveyed is typically in the range of 2–3% annually, a 300,000 member test population would produce an annual mortality rate of 6000–9,000 deaths, wherein a significant number of deaths would have been caused by each of the major underlying causes of death.

One of the further features of the present invention comprises the step of waiting until a substantial number of deaths have occurred in the test population and then selecting those individuals as the ones for whom the biomarker values are to be determined initially. In addition, a group of still living test members may then be selected from the remainder of the test population. Because of the need to balance the need for large enough numbers of samples to obtain statistically significant results with the need to control costs, the subject system provides a practical method of limiting the analytical measurement costs to only those samples that will tend to provide the most information for the least cost. Naturally, as more and more deaths occur in the test population, larger and larger numbers of samples will be analyzed over time. However, the value of the data obtained, from the point of view of establishing more and more reliable quantitative predictions of future health, will be more or less commensurate with the cost of acquiring the additional biomarker values. This is another of the many special features of the present invention that distinguishes it from any known prior art system. This technique of postponing sample analysis permits postponement of cost until the results obtained tend to have greater practical value.

Upon selecting the samples to be analyzed, the biomarker values may be determined using well known methodologies. Since a large number of samples are to be analyzed with each being measured for a large number of biomarker values, many, if not most, of these measurements are typically made using a multi-channel analyzer, for example, the BMD/Hitachi Model 747-100 such as manufactured by the Boehringen Mannheim Corp. of Indianapolis, Ind. Such analyzers can be designed to measure the biomarker values of selected large sets of biomarkers simultaneously using relatively small quantities of the total sample. For example, the quantity of blood collected is typically about 15 ml, whereas only about 10–30 μl may be required per analytical measurement. Similarly, the quantity of urine collected is typically about 50 ml, whereas a quantity of about 100 μl is required for the analysis. Appropriately small quantities of other biological samples may also be used.

Since, in the representative embodiments, physically-preservable biological samples may be used, and since only relatively small analytical sample quantities may be used for taking measurements at any arbitrarily selected time, typically long after the sample has been collected, the subject methodology may be effectively applied using any biomarker that is detectable within a given sample. For example, although the system may be used initially to analyze what are currently deemed to be the more significant biomarkers, the system may be readily adapted to include other biomarkers that are not yet recognized to have significance for predicting future health. In principle, with adequate time and economic resources, every biomarker that is detectable in the preserved biological samples may ultimately be measured.

Although it may be desirable to acquire substantially complete sets of biomarker values for each member of the test population, this is typically very difficult to realize especially if the samples are to be longitudinally collected from a wide, geographically dispersed population base. Using conventional statistical analysis methodology, in which an incomplete set of data is typically discarded and not used at all, substantial quantities of data ultimately covering a large fraction of the initial test population would need to be discarded. This can result in a substantial waste of resources and severe degradation of the quality of the results generated by the remaining data. The subject computer-based methodology includes a feature that provides a means of using substantially all data collected, by using a statistically verifiable technique for filling in the "missing values." This is a particularly useful aspect of the subject methodology, which is based on collecting what amounts to huge quantities of data, as compared with any prior art studies, for very large numbers of test members from a test population that is widely dispersed geographically. Acquisition of comprehensive data from a diverse large test population is particularly desirable so as to obtain biomarker values from members having widely divergent dietary and lifestyle practice representative of the entire human experience.

For the purpose of describing the present invention, the following terminology is explained herein:

A "specified biological condition" may, for example, refer to any one of the following:

a specified disease, for example, as classified in *International Statistical Classification of Diseases and Related Health Problems*, supra. (e.g., diabetes mellitus);

a specified medical or health condition or syndrome (e.g., hypertension, as generally defined by deviations of biomarker or biomarker set values from the usual normal distributions);

a specified medical event and its sequelae (e.g., ischemic stroke and subsequent death, or non-death and stroke-related partial paralysis and related conditions; myocardial infarction and subsequent death, or non-death and MI-related conditions);

premature death from any cause (premature death at an age earlier than the mean age at death as projected from the person's gender and age at first evaluation);

death at a specified age;

a newly defined category based on having or acquiring a specified set of biomarker values for a specified set of biomarkers.

Acquisition or onset of the specified biological condition refers to the situation wherein a person does not have the specified biological condition at the time of a given evaluation, but who subsequently experiences the specified biological condition, in which case the person is said to have acquired the specified biological condition with onset being defined as occurring when the person acquired that specified biological condition.

For a specified biological condition and for a population of persons who do not have, or have not had, the specified biological condition, there are two complementary subpopulations, identified as Group D and Group $\overline{D}$, and described as follows:

Group D: That subpopulation of persons who will acquire the specified biological condition within a specified timeframe. As used here, specified timeframe can refer to a specified interval of calendar time (e.g., "the next five years"), to a specified age interval (e.g., "between 65 and 70 years of age"), or to a similar specific time or age interval.

Group $\overline{D}$: That subpopulation of persons who will not acquire the specified biological condition within the specified timeframe.

These subpopulations of subjects are partially characterized by a specific longitudinal pattern of data on a (possibly large) number of biomarkers. A longitudinal pattern includes not only the level or tissue concentration of a biomarker, but also changes in the level. If one knows which longitudinal patterns of biomarkers partially characterize the subpopulations, and has the necessary data from a specific person, that person can be classified into one of two complementary groups, based upon whether the person is projected to belong to Group D or to Group $\overline{D}$:

Group PD: That group of persons who, at the beginning of the specified timeframe, are predicted to acquire the specified biological condition within the specified timeframe, i.e., projected to belong to Group D. These persons are described as having a prescribed high probability of acquiring the specified biological condition within the specified timeframe.

Group $\overline{PD}$: That group of persons who, at the beginning of the specified timeframe, are predicted not to acquire the specified biological condition within the specified timeframe, i.e., projected to belong to Group $\overline{D}$. These persons are described as having a prescribed low probability of acquiring the specified biological condition within a specified timeframe.

The term "prescribed high probability" may vary in magnitude from having a probability as low as a few percent, perhaps even as low as 1% or less, or may be as high as 10%, 20%, 50%, or even substantially higher, depending on the specified biological condition. For example, the increased risk of acquiring lung cancer due to smoking may be perceived by many as a significant and preferably avoidable risk, even though the actual several-fold increase in risk that is caused by smoking may only be in the range of a 5–10% probability for acquiring lung cancer as far as 15–20 years or more into the future. In any case, for each specified biological condition for which the system is applied, a quantifiably prescribed probability may be determined. The "prescribed low probability" may be specified simply as the probability of not being in the high risk group for acquiring the specified biological condition or, alternatively, the term may be separately specified as a concrete value.

At the point when a statistically adequate number of the members of the test population can be identified as belonging to Group D or Group $\overline{D}$, the biomarker values of the members of Group D may be compared with members of Group $\overline{D}$ using the subject methodology, so as to determine a statistical procedure for classifying members into Groups PD and $\overline{PD}$ or for estimating the probability, for each member of the test population, of acquiring the specified biological condition within the specified time period or age interval, i.e., the probability of belonging to Group PD or the probability of belonging to Group $\overline{PD}$. In a representative embodiment of the subject invention, the statistical procedure for classifying members into Groups PD and $\overline{PD}$ will be a form of a discriminant analysis procedure as described below; the procedure may be referred to as a "discriminant procedure" or "discrimination procedure." A "statistically adequate number" may be defined as one for which the total number of biomarkers used in the analysis and the total number of test members for which the biomarker values are available are each large enough such that convergence is achieved for the computational procedures used in the subject methodology.

A discrimination procedure has two relevant error rates:
(1) Proportion of false positives, i.e., the proportion of future subjects who will be classified in Group PD but who actually belong to Group $\overline{D}$.
(2) Proportion of false negatives, i.e., the proportion of future subjects who will be classified in Group $\overline{PD}$ but who actually belong to Group D.

A representative embodiment of the subject invention will incorporate methodology for obtaining accurate estimate of these two error rates.

A representative embodiment of the subject invention consists of three phases, each with multiple steps. The three phases are:

Phase I. Establish Evaluation Methodology and Select Biomarkers for Consideration.

Phase II. Reduce the Candidate Biomarkers to a Set of Select Biomarkers that have Discriminatory Power and Perform Mixed Model Estimation of the Covariance Structure and Predicted Values.

Phase III: Calculate the Discriminant Functions Using Estimated Means and Predicted Values and Compute Logistic Predicted Values for each Subject; Estimate Error Rates for the Discriminant Functions.

Each Phase has multiple steps. Within a phase some groups of steps are iterative; that is, a specific set of steps may be repeated a number of times until a specified objective is achieved. A representative embodiment of the Phases and their steps are described in the following paragraphs.

Phase I. Establish Evaluation Methodology and Select Biomarkers for Consideration The following steps would appear in a representative embodiment of the subject invention.
Step 1. Select a methodology for estimating the procedure's error rates.

The methodology may incorporate any statistically appropriate method of estimating the error rates. Two methods, of many that may be used, are: Training sample/validation sample, and subsampling (or "resampling").
Training Sample/Validation Sample Method In the training sample/validation sample approach, the test population is randomly divided into two subsets, identified herein as a "training sample" and a "validation sample. Every subject (member of the test population) is assigned to either the training sample or the validation sample. The data from subjects in the training sample are used in the statistical analyses leading to specification of the discriminant procedure and probability estimation procedure. The data from subjects in the evaluation sample will be used to estimate the discriminant procedure's error rates and the distribution of the probability estimates.
Subsampling Methods "Subsampling" refers to a class of statistical methods, including jackknifing and bootstrapping, that can be used to produce reduced-bias estimates of error rates. In a subsampling method, data from all subjects are used in the statistical analyses leading to specification of the discriminant procedure and/or distribution of probability estimates. Utilizing all the data can lead to a better discriminant procedure and/or probability estimation procedure than would be obtained in the Training Sample/Validation Sample approach, especially: (1) if the test population is not large, or, (2) if the a priori probability of acquiring the biological condition is small, even with a large test population. In the present context, subsampling methods are computationally intensive.

Step 2. Select the "training sample," i.e., the subset of the test population to be used for statistical analyses leading to the discriminant procedure/probability estimation procedure, and the "validation sample," Which is the complementary subset.

If a subsampling method is to be used, data from all subjects are used in the statistical analyses leading to specification of the discriminant procedure and/or distribution of probability estimates. In this case, the "training sample" is the entire test population.

If the Training Sample/Validation Sample method is to be used, the training sample will contain, approximately, a specified proportion of the test population. In many cases the training sample proportion will be 50%; however, other proportions may also be used. The validation sample will contain all subjects not included in the training sample.

The random assignment of subjects to the training sample will typically be stratified on subject age. Subject ages are classified into appropriate intervals; an age-group stratum consists of all subjects whose age falls in the specific age interval. Intervals are selected so that the number of subjects in each stratum is adequate for the statistical analyses. Within an age-group stratum subjects will be randomly assigned to the training sample or validation sample. The randomization is organized to achieve, approximately, the specified proportion of subjects in the training sample. For example, if the training sample is specified to include 75% of the test population, approximately 75% of the subjects would be randomly assigned to the training sample within each age-group stratum. For example, if "65 years$\leq$age<70 years" specifies one age-group stratum, approximately 75% of the subjects in this stratum would be randomly assigned to the training sample.

The validation sample, if any, consists of all test population subjects that are not in the training sample.
Step 3: Compile a list of Potential Biomarkers that are potential discriminators.

The goal of this step is to compile list all reasonable, potentially useful biomarkers, which will be called Potential Biomarkers. In a representative embodiment, the list of Potential Biomarkers will include all recorded, quantitative, personal characteristics of subjects in the test population. The list will include characteristics that do not change over time (e.g., date of birth) as well as time-dependent characteristics, such as body weight or a lab assessment from blood or urine. Non-quantitative characteristics, e.g., the name of the subject's favorite color, will be excluded.

Some of the Potential Biomarkers listed in Step 3 will not be useful for discrimination. The remaining steps of this Phase compile a set of "Candidate Biomarkers," from the Step 3 list of Potential Biomarkers. Each Candidate Biomarker will be selected because there is information from previous research/knowledge, or quantitative evidence from the training sample data, that the biomarker is a potentially useful discriminator. At each step, a biomarker that is selected as a candidate is removed from the list of Potential Biomarkers and moved to the set of Candidate Biomarkers. The reason for removing a selected Candidate Biomarker from the list of Potential Biomarkers: once a biomarker has been selected as a candidate there is no reason to reconsider it; it has already "made the list." At the end of the process, all unselected Potential Biomarkers will be removed from further consideration; only the Candidate Biomarkers will be subjected to additional analyses.

Step 4 Initiate the set of Candidate Biomarkers by including any Potential Biomarkers that, on the basis of previous research and experience, are confidently believed to be related to the specified biological condition.

The objective of this step is to utilize prior information on biomarkers that are potentially important discriminants for the specified biological condition. For example, if the specified biological condition is acquiring coronary heart disease (CHD) within a specified time, previous research has shown that values of serum cholesterol, systolic blood pressure, glucose intolerance, or cigarette smoking (to name just a few) are related to onset of CHD and should be copied from the list of Potential Biomarkers to the list of Candidate Biomarkers.

Any reliable source of information or 'educated guess' may be relied upon to select the subset of biomarkers known or believed to be related to the specified biological condition. Although the identity of the biomarkers initially selected is not critical to determining the identity of the subset that is ultimately selected for use in discrimination, the initial selection of biomarkers that are ultimately confirmed by this system as having the greatest statistical significance for predicting the specified biological condition will assist in providing more rapid convergence to the empirically determined subset. In other words, the more educated the initial selection, the more rapid the convergence.

Step 5. Add to the list of Candidate Biomarkers any Potential Biomarkers that are "statistically significantly" correlated with the "known important" biomarkers from Step 4.

Data from the training sample are used to compute a correlation coefficient between each previously identified Candidate Biomarker (which are "known important" biomarkers) and each Potential Biomarker. Any statistically valid correlation coefficient may be used.

The goal is to identify biomarkers that may be good discriminators. A correlate of a "known important" biomarker may be a better discriminator than the "known important" biomarker itself. At the least, correlates of known important biomarkers should be included in the initial analyses.

If the specified biological condition is actually defined by values of one or more biomarkers, (e.g., hypertension), the defining biomarkers would be "known important" biomarkers and would have been moved to the list of Candidate Biomarkers in Step 4. Correlates of the defining biomarkers would be moved to the list of Candidate Biomarkers in this Step.

"Statistical significance" is used here only as a tool for deciding between "probably important" and "probably unimportant" correlates. In a representative embodiment, a traditional p-value will be computed for a correlation between a Potential Biomarker and a Candidate Biomarker. If p is less than some specified value, e.g., $p<0.05$, or $p<0.01$, the Potential Biomarker is moved to the Candidate Biomarker list.

Step 6. Fit a logistic regression model for each Potential Biomarker, using a binary indicator variable for the specified biological condition as the dependent (Y) variable and age and the Potential Biomarker as the independent (X) variables. Add to the list of Candidate Biomarkers each Potential Biomarker that is "statistically significant" in its logistic regression model.

The objective of this step is to select as Candidate Biomarkers those Potential Biomarkers that are related to the probability of acquiring the specified biological condition, after taking the (linear) effect of age into account. The logistic model expresses the probability of acquiring the specified biological condition as a function of the value of the Potential Biomarker, in conjunction with a subject's age.

A biomarker is selected (or not) on the basis of a marginal p-value for the biomarker's slope in the logistic regression model. As with the correlations above, "statistical significance" is used here only as a tool for deciding between "probably important" and "probably unimportant" discriminators. In a representative embodiment, a traditional p-value will be computed for the slope of a Potential Biomarker. If p is less than some specified value, e.g., $p<0.05$, or $p<0.01$, the Potential Biomarker is moved to the Candidate Biomarker list.

Step 7: Evaluate each longitudinally-assessed Potential Biomarker, using a general linear mixed model ("MixMod") to assess whether longitudinal trends in the biomarker's values are related to acquisition of the specified biological condition. Each Potential Biomarker with a statistically significant longitudinal trend is moved to the list of Candidate Biomarkers.

The goal of this step is to identify biomarkers, other than those previously promoted to Candidate Biomarker status, that have longitudinal trends that are related to the probability of acquiring the specified biological condition.

In a typical embodiment of the subject invention, each model will be created as follows. The dependent variable (Y) in the MixMod contains longitudinal values of the Potential Biomarker. The independent (X) variables for fixed effects are: (1) a binary indicator variable for the specified biological condition, (2) age or another relevant longitudinal metameter such as time since some germane event, visit number, etc., and (3) the interaction between the binary indicator variable for the specified biological condition and the longitudinal metameter. The random effects part of the model includes a random subject increment to the intercept of the population regression line and, in some cases, a random slope with respect to the longitudinal metameter. When two or more random effects are included, the covariance matrix of the random effects is typically unstructured. Age or another relevant longitudinal metameter is included in the model for the same reasons as in Step 6.

If the coefficient corresponding to any X-variable other than age is statistically significant, the Potential Biomarker is moved to the list of Candidate Biomarkers. The remarks on statistical significance in Step 6 are applicable here.

At the end of Steps 4–7, all Potential Biomarkers have been examined and each biomarker with historical or quantitative evidence of utility as a discriminator has been moved to the list of Candidate Biomarkers.

Phase II. Reduce the Candidate Biomarkers to a Set of Select Biomarkers that Have Discriminatory Power and Perform Mixed Model Estimation of the Covariance Structure and Predicted Values Background. Prior art discriminant analysis methodology typically requires relatively precise estimates of the mean vectors, $\mu_i$, and covariance matrices, $\Sigma_i$, of the distributions of the biomarkers (and other variables, such as age and demographics) of the two groups, Group D (i=1) and Group $\overline{D}$ (i=2). The $\mu_i$ are estimated as simple sample means (vectors) and the $\Sigma_i$ are estimated as simple sample covariance matrices, which do not permit adjustment of the mean for important concomitant variables (or "covariates") and does not readily include repeated measures from the same subject. Moreover, prior art discriminant analysis is typically based upon a "casewise deletion" procedure: if a subject has any missing data, all of that subject's data are deleted from the analyses.

Given estimates of the mean vectors, $\mu_i$, and covariance matrices, $\Sigma_i$, and the biomarker (and related data) for a subject in a vector, Y, the traditional discriminant functions (linear if $\Sigma_1=\Sigma_2$, quadratic if $\Sigma_1 \neq \Sigma_2$) are evaluated solely from Y, $\mu_1, \mu_2, \Sigma_1$, and $\Sigma_2$. The only information specific to the particular subject is in the vector Y.

The mixed model procedure, which is the greater part of Phase II, improves the traditional procedure by using a general linear mixed model (MixMod) to model all of $\mu_1, \mu_2, \Sigma_1$, and $\Sigma_2$; the modeled estimates of these parameters are used in the discriminant function rather than the traditional simple, unmodeled estimates. This MixMod procedure makes the following important improvements over traditional discriminant analysis:

The parameters are estimated using a Mixed Model, that:
uses all available data, i.e., does not use casewise deletion;
supports covariate adjustment of the estimated expected values ($\mu_i$), with corresponding adjustment of the estimated covariance matrices $\Sigma_i$, and
supports the utilization of repeated measures (e.g., from annual visits) from the same subject.

This MixMod procedure utilizes model-based estimates of individual random effects and "BLUPs" ("Best Linear Unbiased Predictors"), in addition to or in place of the estimates of the population means $\mu_i$, which can substantially increase the discrimination capability of the discriminant function.

Overview of the Phase II Procedure

As a result of Phase I, each Candidate Biomarker will have historical or quantitative evidence of utility as a discriminator. However, there are substantial correlations among the Candidate Biomarkers. Consequently, a biomarker that, considered by itself, has substantial discriminatory power, may not make a substantial contribution when used in combination with other biomarkers. In addition, the scales of the biomarkers may vary widely.

The objectives of Phase II of the subject procedure are to:

(1) Rescale the biomarker values so that standard deviations of all rescaled biomarkers are on the same order of magnitude (0<standard deviation≦1).

(2) Reduce the possibly long list of Candidate Biomarkers to a smaller number of "Select Biomarkers," each of which contributes substantially to the discriminatory power of the set.

(3) Determine the structure of the expected value of the vector Y of (resealed) biomarker values using a linear model of the form E[Y]=X$\beta$, and estimate $\beta$, a vector of unknown parameters.

(4) Determine the structure of the covariance matrix of the vector Y of (rescaled) biomarker values using a model of the form $\Sigma=Z\Delta Z'+V$, and to estimate the unknown covariance parameters in the matrices $\Delta$ and V.

(5) Estimate the random subject effect vector, $d_{ik}$, and compute the predicted-value vector, $Y_{ki}^{(p)}$ of the k-th subject, as if that subject came from the i-th specified biological condition group; i=1 corresponds to Group D and i=2 corresponds to Group $\overline{D}$.

In a representative embodiment of the subject invention, Step 1 of this Phase is performed once in order to rescale the biomarker data and arrange the data into one data vector (or one variable in a dataset). Steps 2 and 3 are performed iteratively until the set of Select Biomarkers has been selected and the estimates listed above have been computed. Step 4 refines the mixed model and parameter estimates to be used in the discrimination by selecting appropriate models for the covariance matrices.

Step 1. Prepare a dataset in which one variable, "RespScal," contains scaled values (including longitudinal measures) of all Candidate Biomarkers from all subjects.

The scaling is performed separately for each biomarker. Each biomarker value is divided by the sample standard deviation of that biomarker. Thus, the standard deviation of the scaled values of each biomarker is 1.00. In a representative embodiment of the subject invention the one variable of biomarker values may be named "RespScal", an abbreviation of "Response—Scaled"). The sample standard deviation of RespScal is also approximately 1.00. This scaling facilitates convergence of the iterative procedure in subsequent mixed model computations.

Step 1 is executed only once. Initially, all Candidate Biomarkers have data in RespScal and are considered members of the set of Select Biomarkers. Non-discriminating biomarkers will be removed from the Select Biomarkers in Steps 2–3.

Step 2: Fit a general linear mixed model (MixMod) using the specifications listed below; obtain estimates of the parameter matrices $\beta$, $\Delta$, and V, obtain estimates of each subject's random subject effects, $d_{ik}$, and each subject's "predicted values," $Y_{ik}^{(min)}$ and $Y_{ik}^{(avg)}$ as if the subject were in each specified biological condition group, i=1, 2.

In a representative embodiment of the subject invention the following are specifications of the MixMod:

Dependent (Y) variable: RespScal;
Independent (X) variables and their coefficients ($\beta$):
"Biological Condition Status," an indicator variable for the status of the specified biological condition (classification variable); Biological Condition Status=1 if the corresponding element of Y contains information about a subject from Group D and Biological Condition Status=0 otherwise.
Biomarkers' indicator variables (classification variables);
Biological Condition Status×Biomarkers' indicator variables (classification variables);
Age (in years, centered at approximately the overall mean age of subjects; continuous variable);
Random effects variables ($Z_k$) and random coefficients (effects, $d_{ik}$):
Subject×Biomarker indicator variables (part of $Z_k$) and corresponding random effects (intercept increments; part of $d_{ik}$).

The random subject effect for a specific biomarker is constant across that subject's multiple visits, which generates correlations among repeated measurements of that biomarker for that subject. Note that the model assumes $E[d_{ik}]=0$ and $V[d_{ik}]=\Delta$.

Covariance matrix, $V_k=V(\epsilon_{kb})$, of the vector $\epsilon_{kb}$ of biomarker random error terms, $\epsilon_{kbv}$, for the k-th subject at the v-th longitudinal evaluation of the b-th scaled Candidate Biomarker. This covariance matrix has one row and one column for each longitudinal evaluation of each biomarker for the k-th subject. Note that the model also assumes $E[\epsilon_{kb}]=0$.

The primary interpretation of $\epsilon_{kbv}$ is as a "random measurement error term," representing variation, from one evaluation to another, of a value of the scaled Candidate Biomarker about subject k's age-dependent mean value for that scaled Candidate Biomarker. With this interpretation, it is often reasonable to assume that values of $\epsilon_{kbv}$ are homoscedastic and are uncorrelated, i.e., $Cov(\epsilon_{kbv}, \epsilon_{k'b'v'})=0$ if $(k,b,v) \neq (k',b',v')$. If the elements of Y are sorted by k (subject ID), b (biomarker ID), and v ("visit" or evaluation number or age of subject), then a reasonable model for $V_k$ in many cases is $V_k=\text{BlockDiag}(V_{kb})=\text{BlockDiag}(V_{k1}, V_{k2}, \ldots)$, where $V_{kb}=\lambda_b I$ and $\lambda_b=V(\epsilon_{kbv})$, the variance of measurement errors for scaled values of the b-th Candidate Biomarker, which variance is assumed to be the same for all subjects (k) and all evaluations (v).

Note that the scaling of RespScal implies that each variance, $\lambda_b$, will be less than 1.00. The extent to which the variance is less than 1.00 depends upon the magnitudes of the fixed effects (a high $R^2$ leads to a smaller estimated variance) and the magnitudes of the variances of the random effects (diagonal elements of $\Delta$).

Note the above combination of $Z_k$, $d_k$, $V_k=\text{BlockDiag}(V_{kb})$ and $V_{kb}=\lambda_b I$ generate a highly structured, extended compound symmetric model for $\Sigma_{ik}$. To illustrate the point in an example when the same covariance parameters apply to both Group D and Group $\overline{D}$, let $d_k=[d_{kb}]=[d_{k1}, d_{k2}, \ldots]'$ be the vector of random effects for the k-th subject and b-th scaled biomarker, let $V(d_k)=\Delta=[\delta_{b\;b'}]$, where $\delta_{b\;b'}=\text{Cov}(d_{kb}, d_{kb'})$ where b and b' index possibly different scaled biomarkers, let $Z_k$ contain indicator variables for the scaled biomarkers, and let $V_{kb}=\lambda_b I$. Then $\Sigma_k=Z_k\Delta Z'_k+V_k=[\Sigma_{k,b\;b'}]$, where $\Sigma_{k,b\;b'}=\delta_{b\;b'}J+\lambda_b I=$ covariance matrix of multiple measurements from scaled biomarker b, and $\Sigma_{k,b\;b'}=\delta_{b\;b'}J=$ covariance of scaled biomarkers b and b' evaluated on the same occasion or on different occasions. (Each element of the square matrix J equals 1.)

The process of fitting the mixed model produces estimates of:

The model's parameters, $\beta$, $\Delta$, and parameters of $V_k$. If the model assumes different covariances for the two Biological Condition Status groups, the model produces separate estimates of the covariance parameters in $\Delta_i$ and $V_{ik}$.

The expected value of each subject's data vector, $\mu_{ik}$, (subject k being in Biological Condition Status group i), The expected value of each subject's data vector, $\mu_{i'k}$, as if the subject were in the other response group (i'), Each subject's random subject effect in the subject's actual treatment group (i), $d_{ik}$, and also as if the subject were in the other response group (i'), $d_{i'k}$.

Each subject's "predicted values," in the subject's actual treatment group (i): $Y_{ik}^{(p)}$, and also as if the subject were in the other response group (i'): $Y_{i'k}^{(p)}$.

The subject's covariance matrix, $\Sigma_k$. If the model assumes different covariances for the two Biological Condition Status groups, the model produces separate estimates of the covariance matrices $\Sigma_{ik}$.

Step 3: Delete the biomarker that has the least apparent discriminant power and re-fit the mixed model.

A biomarker that will be an effective discriminant should have a large (statistically significant) Biological Condition Status×Biomarker fixed effect. In contrast, a large Biomarker main effect is not relevant here: a large Biomarker main effect—indicating differences among biomarker means—can arise simply because the biomarkers are different types of variables and have different means (on the rescaled axis). In contrast, a large Biological Condition Status×Biomarker effect indicates that the biomarker mean for the Biological Condition Status=0 (Group $\overline{D}$) is significantly different from biomarker mean for the Biological Condition Status=1 (Group D) mean for the same biomarker. Such a difference should make an important contribution to the discrimination procedure.

If each current Selected Biomarker has a statistically significant Biological Condition Status×Biomarker fixed effect, Step 3 is completed and we move to Step 4. If one or more current Select Biomarkers has a not-statistically-significant Biological Condition Status×Biomarker fixed effect, the biomarker with the least statistically significant (largest p-value) Biological Condition Status×Biomarker fixed effect is removed from the data vector, Y, and we return to Step 2 where a MixMod is fitted to the reduced data vector.

The strategy being implemented in Step 3 is an analog of a "backwards elimination" procedure in the stepwise regression context. An alternative is to implement an analog of "forward selection," in which one initially includes only a very small number of clearly effective discriminants (biomarkers) in the data vector and model and, at each subsequent step, adds one more biomarker.

Step 4: Determine the structures of the covariance parameter matrices, $\Delta_p$ and $V_{ik}$.

Discriminant analysis methodology uses both the expected values of the biomarkers and the covariance matrices of the biomarkers (some of which may be evaluated longitudinally) separately for each Biological Condition Status group, D and $\overline{D}$. Recall that the list of Select Biomarkers, including possible longitudinal assessments, already will have been finalized in Step 3. As noted above, a MixMod incorporates assumptions that lead to the following structure for the covariance matrices: $\Sigma_{ik}=Z_{ik}\Delta_i Z'_{ik}+V_{ik}$, where i indexes Biological Condition Status group (i=1 for Group D, for i=2 for Group $\overline{D}$) and k indexes subjects. In addition, the covariance parameter matrices $\Delta_i$ and $V_{ik}$ may have structure that can be exploited in the analysis, especially when $\Sigma_{ik}$ is very large, i.e., when there are many biomarkers and/or many longitudinal assessments of one or more biomarkers.

The objective of Step 4 is to determine the structure of the covariance parameter matrices $\Delta_i$ and $V_{ik}$ for use in the Phase III discriminant analyses. Estimates of large, structured covariance parameter matrices tend to be more precise than estimates of unstructured covariance parameter matrices. A more precise estimate of $\Delta_i$ and/or $V_{ik}$ leads to a more precise estimate of $\Sigma_{ik}=Z_{ik}\Delta_i Z'_{ik}+V_{ik}$, thence to more precise estimates of $\beta$, the $d_{ik}$, and the $Y_{ik}^{(p)}$, and to more precise values of the discriminant function.

The overall structure of $\Sigma_{ik}$ must take into account the following types of covariances/correlations:

Type ADB: Covariances/correlations among different biomarkers evaluated at the same time point;

Type ALESB: Covariances/correlations among longitudinal evaluations of a single biomarker;

Type BTBEL: Covariances/correlations between two biomarkers, evaluated longitudinally, i.e., covariances/correlations between any pair of biomarkers, one evaluated at one time and the other evaluated at a different time.

In a representative embodiment of the subject invention, the structures described in Step 2, above, or extensions of these structures may be useful.

In a representative embodiment of the subject invention, the techniques described in Tangen, Catherine M., and Helms, Ronald W., (1996), "A case study of the analysis of multivariate longitudinal data using mixed (random effects) models," presented at the 1996 Spring Meeting of the International Biometric Society, Eastern North American Region, Richmond, Va., March, 1996, are used to explore covariance/correlation structures for longitudinal multivariate data. Selecting a covariance model typically requires fitting a number of MixMods, typically using the same expected-value model and varying the covariance model. Models may be compared via Log Likelihood statistics (assuming underlying normal distributions). Covariance structures may also be compared graphically using techniques developed by Ronald W. Helms at the University of North Carolina, e.g., Grady, J. J. and Helms, R. W. (1995), "Model Selection Techniques for the Covariance Matrix for Incomplete Longitudinal Data." *Statistics in Medicine*, 14, 1397–1416.

Phase III: Calculate Discriminant Functions Using Estimated Means and Predicted Values and Compute Logistic Predicted Values for each Subject; Estimate Error Rates for the Discriminant Functions Background. The objective of Phase III is to "predict" which "population" or group a subject will belong to, Group D or Group $\overline{D}$:

Group D: That subpopulation of persons who will acquire the specified biological condition within a specified timeframe.

Group $\overline{D}$: That subpopulation of persons who will not acquire the specified biological condition within the specified timeframe.

A subject is classified by placing the subject into one of the following two groups:

Group PD: That group of persons who, at the beginning of the specified timeframe, are predicted to acquire the specified biological condition within the specified timeframe, i.e., projected to belong to Group D. These persons are described as having a prescribed high probability of acquiring the specified biological condition within the specified timeframe.

Group $\overline{PD}$: That group of persons who, at the beginning of the specified timeframe, are predicted not to acquire the specified biological condition within the specified timeframe, i.e., projected to belong to Group $\overline{D}$. These persons are described as having a prescribed low probability of acquiring the specified biological condition within a specified timeframe.

A second objective is to estimate the probabilities that a subject will belong to Groups D and $\overline{D}$.

The technology for achieving the first objective—classifying a subject into one of the two groups—uses discriminant procedures that are modifications of traditional discriminant analysis. The estimates of the probability that the subject will be in the group of subjects that will acquire the specified biological condition is obtained from a modification of traditional logistic regression, (1) using the discriminant function values as regressors and (2) using the discriminant variables as regressors.

As noted in the background of Phase II, prior art discriminant analysis methodology typically utilizes naive estimates of the mean vectors, $\mu_i$, and covariance matrices, $\Sigma_i$, of the distributions of the biomarkers of the two groups. Moreover, prior art discriminant analysis is typically based upon a "casewise deletion" procedure: if a subject has any missing data, all of that subject's data are deleted from the analyses.

The mixed model procedure, described in Phase II, improves the traditional procedure by using a general linear mixed model (MixMod) to model all of $\mu_1$, $\mu_2$, $\Sigma_1$, and $\Sigma_2$; the modeled estimates of these parameters are used in the discriminant function rather than the traditional simple, unmodeled estimates. The use of the mixed model permits the present procedures to make the following important improvements over traditional discriminant analysis: The parameters are estimated using all available data, i.e., does not use casewise deletion. The procedure supports covariate adjustment of the estimated expected values ($\mu_i$), with corresponding adjustment of the estimated covariance matrices $\Sigma_i$. And the procedure supports the utilization of repeated measures (e.g., from annual visits) from the same subject.

Perhaps more importantly, the use of the mixed model permits the present procedures to utilize model-based estimates of individual random effects and "BLUPs" ("Best Linear Unbiased Predictors"), in addition to or in place of the estimates of the population means $\mu_i$, which can substantially increase the discrimination capability of the discriminant function.

The form of the present discriminants are formally identical to the traditional discriminant based upon multivariate normality. Some notation is useful; let:

$f_i$ denote the density function of the distribution of the vector Y of discriminant variables for a subject from group i, evaluated using "estimates" of $\mu_i$ and $\Sigma_i$, i=1 for Group D or Group PD, i=2 for Group $\overline{D}$ or Group $\overline{PD}$;

$p_i$ denote the a priori probability that a subject will come from group i, i=1 for Group D, i=2 for Group $\overline{D}$. The values of the $p_i$ are often known from historical data or other research. If the values of the $p_i$ are unknown, the proportions of the subjects in the two groups may be used as estimates of the $p_i$.

Then a subject of unknown group with vector Y of discriminant function values would be classified into group 1 (Group PD) if $Ln[f_1(Y)/f_2(Y)] > Ln[p_2/p_1]$ and would be assigned to group 2 (Group $\overline{PD}$) otherwise.

In Phase II one will have decided whether one can reasonably assume the two groups have equal covariance matrices, $\Sigma_1 = \Sigma_2 = \Sigma$. In that case, the present discriminant procedure reduces to use of a linear discriminant function of the following form:

$$D(Y) = [Y - \tfrac{1}{2}(\mu_1 + \mu_2)]' \Sigma^{-1}(\mu_1 - \mu_2) - Ln[p_2/p_1]$$

where the $\mu_i$ and $\Sigma_i$ are replaced by "appropriate" estimates to be discussed below. One compares D(Y) vs. 0. If, in Phase II, it was decided that $\Sigma_1 \neq \Sigma_2$, the discriminant procedure reduces to use of a quadratic discriminant function of the following form:

$$Q(Y) = \tfrac{1}{2}ln(|\Sigma_2|/|\Sigma_1|) - \tfrac{1}{2}(Y-\mu_1)'\Sigma_1^{-1}(Y-\mu_1) + \tfrac{1}{2}(Y-\mu_2)'\Sigma_2^{-1}(Y-\mu_2) - Ln[p_2/p_1]$$

where the $\mu_i$ and $\Sigma_i$ are replaced by "appropriate" estimates to be discussed below. One compares Q(Y) vs. 0.

In either case, the "appropriate" estimates come from the mixed model procedure in Phase II and may or may not include random subject effects.

Phase III Procedure

The steps of Phase III of the procedure are described below. It is assumed that data are available from one or more "new" subjects, i.e., subjects whose group membership is unknown and that were not used in the Phase II mixed model computations. In Steps 1–2 we shall consider one subject at a time. Some additional notation is useful. Let i=1 for Group D or Group PD, i=2 for Group $\overline{D}$ or Group $\overline{PD}$ and let:

Y denote the vector of values of the discriminant variables for one new subject. The elements of Y are scaled as RespScal was scaled in Phase II.

$X_i$ denote the matrix of values of the independent variables used in the final Phase II mixed model, as if the subject were in group i, i=1, 2. Note that the rows of $X_i$ correspond to the rows (elements) of Y.

$Z_i$ denote the matrix of values of the random effect variables used in the final Phase II mixed model, as if the subject were in group i, i=1, 2. Note that the rows of $Z_i$ correspond to the rows of Y.

$\hat{\Delta}_i$ denote the estimated covariance matrix of the random effects from group i, i=1, 2, from the final Phase II mixed model. Note that in many cases the mixed model reduced to a single covariance for the random effects, i.e., $\hat{\Delta}_1 = \hat{\Delta}_2 = \hat{\Delta}$.

$\hat{V}_i$ denote the estimated covariance matrix of the random residuals or "error terms" from group i, i=1, 2, from the final Phase II mixed model. Note that in many cases the mixed model reduced to a single covariance matrix, i.e., $\hat{V}_1 = \hat{V}_2 = \hat{V}$.

$\hat{\Sigma}_i = Z_i \hat{\Delta}_i Z_i' + \hat{V}_i$ denote the estimated covariance matrix of Y, from the final Phase II mixed model, as if the new subject came from group i, i=1, 2. Note that in many cases the mixed model reduced to a single covariance matrix, i.e., $\hat{\Sigma}_1 = \hat{\Sigma}_2 = \hat{\Sigma}$.

Step 1: Using results from the Phase II mixed model, classify all subjects in the validation sample and estimate the error rates of multiple candidate discriminant procedures, one based on "estimated values," and others based upon "predicted values" utilizing various combinations of the estimated random subject effects. The procedure with the lowest estimated error rate is selected procedure and is referred to as the "apparently most reliable procedure."

If the original study population was divided into a "training sample" and a "validation sample," use the validation sample in the following; otherwise use the training sample as the "validation sample." Estimate the following quantities for each subject in the validation sample, separately, as if the subject came from each group.

$\hat{Y}_i = X_i \hat{\beta}$, the "estimated value" of Y, as if the subject came from group i, i=1, 2. $\hat{d}_i = \hat{\Delta}_i Z_i' \hat{\Sigma}_i^{-1}(Y - X_i \hat{\beta})$, the estimate of the subject's random subject effect, as if the subject came from group i, i=1, 2.

$\hat{d}_{min} = \hat{d}_1$ if $\hat{d}_1' \hat{\Delta}_1^{-1} \hat{d}_1 \leq \hat{d}_2' \hat{\Delta}_2^{-1} \hat{d}_2$; otherwise $\hat{d} = \hat{d}_2$. $\hat{d}_{min}$ may be thought of as the "minimum" of $\hat{d}_1$ and $\hat{d}_2$, or the "minimum (over groups) random subject effect" estimate.

$\hat{d}_{avg} = (\hat{d}_1 + \hat{d}_2)/2$. $\hat{d}_{avg}$ may be thought of as the "average" of $\hat{d}_1$ and $\hat{d}_2$, or the "average (over groups) random subject effect" estimate.

$Y_i^{(min)} = X_i \hat{\beta} + Z_i \hat{d}_{min}$, the subject's "predicted values," as if the subject came from group i, i=1, 2, but using the "minimum" random subject effect estimate.

$Y_i^{(avg)} = X_i \hat{\beta} + Z_i \hat{d}_{avg}$, the subject's "predicted values," as if the subject came from group i, i=1, 2, but using the "average" random subject effect estimate.

In the above and below, i=1 for Group D or Group PD, i=2 for Group $\overline{D}$ or Group $\overline{PD}$.

Classification based upon the estimated values, $\hat{Y}_i$.

If the decision $\Sigma_1 = \Sigma_2 = \Sigma$ was made in Phase II, evaluate the linear discriminant function, D(Y) (above), substituting $\hat{Y}_i$ for $\mu_i$ and $\hat{\Sigma}$ for $\Sigma$. Assign the subject to group 1 (Group PD) if D(Y)$\geq$0; otherwise assign the subject to group 2 (Group $\overline{PD}$)

If the decision $\Sigma_1 \neq \Sigma_2$ was made in Phase II, evaluate the quadratic discriminant function, Q(Y) (above), substituting $\hat{Y}_i$ for $\mu_i$ and $\hat{\Sigma}_i$ for $\Sigma_i$, i=1, 2. Assign the subject to group I (Group PD) if Q(Y)24 0; otherwise assign the subject to group 2 (Group $\overline{PD}$).

Classification based upon the "minimum" random subject effects and predicted values, $Y_i^{(min)}$.

If the decision $\Sigma_1 = \Sigma_2 = \Sigma$ was made in Phase II, evaluate the linear discriminant function, D(Y) (above), substituting $Y_i^{(min)}$ for $\mu_i$ and $\hat{\Sigma}$ for $\Sigma$. Assign the subject to group 1 (Group PD) if D(Y)$\geq$0; otherwise assign the subject to group 2 (Group $\overline{PD}$).

If the decision $\Sigma_1 \neq \Sigma_2$ was made in Phase II, evaluate the quadratic discriminant function, Q(Y) (above), substituting $Y_i^{(min)}$ for $\mu_i$ and $\hat{\Sigma}_i$ for $\Sigma_i$, i=1, 2. Assign the subject to group I (Group PD) if Q(Y)$\geq$0; otherwise assign the subject to group 2 (Group $\overline{PD}$).

Classification based upon the "average" random subject effects and predicted values, $Y_i^{(avg)}$:

If the decision $\Sigma_1 = \Sigma_2 = \Sigma$ was made in Phase II, evaluate the linear discriminant function, D(Y) (above), substituting $Y_i^{(avg)}$ for $\mu_i$ and $\hat{\Sigma}$ for $\Sigma$. Assign the subject to group 1 (Group PD) if D(Y)$\geq$0; otherwise assign the subject to group 2 (Group $\overline{PD}$).

If the decision $\Sigma_1 \neq \Sigma_2$ was made in Phase II, evaluate the quadratic discriminant function, Q(Y) (above), substituting $Y_i^{(avg)}$ for $\mu_i$ and $\hat{\Sigma}_i$ for $\Sigma_i$, i=1, 2. Assign the subject to group 1 (Group PD) if Q(Y)$\geq$0; otherwise assign the subject to group 2 (Group $\overline{PD}$).

After each subject in the validation sample (as defined above) is classified, compute a 2×2 table, similar to the following, for each of the three procedures (based on estimated values or based upon predicted values):

| Numbers of subjects in the validation sample tabulated by actual and classified membership | Subject was classified as a member of Group: | |
| --- | --- | --- |
| in D. | $\overline{PD}$ | PD |
| Subject was actually a member of Group: $\overline{D}$ | $N_{11}$ = Number of true negative classifications | $N_{12}$ = Number of false positive classifications |
| D | $N_{21}$ = Number of false negative classifications | $N_{22}$ = Number of true positive classifications |

Further, compute separately for classification based on estimated values and for classification based upon predicted values:

$N_{i+} = N_{i1} + N_{i2}$ $r_{FP} = N_{12}/N_{1+}$ = false positive error rate = proportion of false positive classifications $r_{FN} = N_{21}/N_{2+}$ = false negative error rate = proportion of false negative classifications $r_{tot} = (N_{12} + N_{21})/(N_{1+} + N_{2+})$ = total error rate = proportion of false classifications In a typical embodiment of the subject invention, one will compare the three types of classification procedures, i.e., the one based on estimated values, $\hat{Y}_i$, the one based on "minimum" predicted values, $Y_i^{(min)}$, and the one based on "average" predicted values, $Y_i^{(avg)}$, to determine the "apparently most reliable procedure." Some considerations in the selection process are:

If a false negative classification has substantially more serious consequences than a false positive classification, select the procedure with the smaller false negative error rate, $r_{FN}$. This situation could arise, for example, if Group D is the subpopulation of persons who will suffer a myocardial infarction ("MI") within a specified five year age group. A false negative classification, failure to warn a person of a high MI probability, could have more serious consequences than a false positive classification, warning a low-probability person that they have a high MI probability.

Conversely, if a false positive classification has substantially more serious consequences than a false negative classification, select the procedure with the smaller false positive error rate, $r_{FP}$.

When there is no a priori reason to assign greater seriousness to either a false negative or a false positive classification, select the procedure with the smaller total error rate, $r_{tot}$.

The procedure selected as the apparently most reliable procedure is used to classify subjects into the two groups, Group PD and Group $\overline{PD}$.

Step 2. Use two types of logistic regression to compute estimates of the probability that a newt subject will belong to each group.

The data from the training sample are used to fit a logistic regression model in which the value of the discriminant function (D(Y) if linear, Q(Y) if quadratic) for each subject is used as the independent ("X") variable and the Biological Condition Status (indicator variable for membership in Group D) as the dependent ("Y") variable. The model is used, together with inverse logistic transform, to compute for each subject an estimate of the probability that the subject will belong to Group D.

In a separate calculation, the data from the training sample are used to fit a logistic regression model in which the biomarkers used in the discriminant function, together with the final mixed model covariates (variables in X), are incorporated as independent ("X") variables and the Biological Condition Status (indicator variable for membership in Group D) as the dependent ("Y") variable. In addition to obtaining the usual logistic regression model estimates, the model is used, together with inverse logistic transform, to compute for each subject an estimated probability that the subject will belong to Group D. When longitudinal data are used, the model is used to estimate the probability that the subject will belong to Group D at the end of the specified period. One can use a generalized estimating equation approach with a logistic link function to accommodate correlations among the multiple binomial outcomes from one subject.

The predicted probabilities from these two models can provide interesting interpretations of discriminant function values.

While the subject algorithm is the preferred embodiment for determining the discriminant function to be used in the subject, it is to be understood that this algorithm is provided solely for the purpose of illustrating the preferred embodiment of the subject invention, and in no case is it to be understood that the subject invention is limited to the steps or substeps of the algorithm described herein. For example, it is to be understood that in the art and field of discriminant analysis methodology, there are other types of discriminant functions, e.g., so-called "optimal discrimination," other types of regression, e.g., nonlinear mixed models, etc., that may also be used while falling fully within the scope and spirit of the subject invention.

This invention will now be described in detail with respect to specific representative embodiments thereof, the materials, apparatus and process steps being understood as examples that are intended to be illustrative only. In particular, the invention is not intended to be limited to the statistical methods, materials, conditions, process parameters, apparatus and the like specifically recited herein.

AN EXAMPLE OF THE PREFERRED EMBODIMENT

The attached tables and Figure present the results of an illustrative analysis of data using the methods and procedures of the subject invention.

The data used as a basis for this example were obtained from a database including patients for whom Sickle Cell data are acquired on an annual basis. Some patients have data from three consecutive visits. However, since patients typically cannot be compelled to participate annually, the database includes many patients for whom data are available from only one or two annual visits. Database information that was used here included demographic data, clinical chemistry data, and hematological data.

The specified biological condition of interest (the "disease" or "affliction") in this example was an occurrence of a painful crisis that required hospitalization. At each annual visit the subject is asked (and records are checked to determine) if the subject had a painful crisis that required hospitalization in the preceding year. Each subject who reported having had a hospitalization for a painful crisis at any visit (any year) is a member of the "Diseased" group (Group D); all other subjects are members of Group $\overline{D}$.

Whenever a subject had had a painful crisis that required hospitalization in the preceding year, all data that were collected after the hospitalization for the painful crisis, in the same year or in later years, were excluded from the analysis. This mimics the procedure that would be used if the outcome were death or occurrence of a chronic, incurable disease. The variable that records a subject's Group D membership (e.g., diseased or not, afflicted or not) is named the "Disease Status" variable.

The following is an example of the statistical analysis procedures using the sickle cell data. For reasons of confidentiality, the data used in this example are artificial and do not come from a real study or from real subjects. However, the data are similar to data that could have been obtained in a study of real subjects.

Phase I. Establish Evaluation Methodology and Select Biomarkers for Consideration Step 1. Select a methodology for estimating the procedure's error rates.

Step 2. Select the "training sample," i.e., the subset of the test population to be used for statistical analyses leading to the discriminant procedure/probability estimation procedure, and the "validation sample," which is the complementary subset.

The Training Sample/Validation Sample Method was chosen for this example. Patients were randomly assigned to one of the two samples. The training sample was used to create the discriminant function; the validation sample was used to evaluate the accuracy of the discriminant function.

The training sample included information from 641 "annual" evaluations from 481 subjects, or about 1.3 annual evaluations per subject. However, not all biomarkers were assessed, even when a subject made a visit. For an extreme example, only 88 values of Direct Bilirubin (variable L_DBILI) were available from only 80 subjects.

Step 3. Compile a list of Potential Biomarkers that are potential discriminators.

In this case, blood pressures, all available demographic data, clinical chemistry data, and hematological data were used as potential discriminators. The Potential Biomarkers are listed in Table 2.

Step 4: Initiate the set of Candidate Biomarkers by including any Potential Biomarkers that, on the basis of previous research and experience, are confidently believed to be related to the specified biological condition.

In the example, Platelet Count (or "Platelets") was taken as a "known" biomarker for Disease Status, hospitalization for a pain crisis.

Step 5: Add to the list of Candidate Biomarkers any Potential Biomarkers that are "statistically significantly" correlated with the "known important" biomarkers from Step 4.

Biomarkers were selected that were correlated with the "knower important" biomarker, platelets, from Step 2. A summary of these correlations is shown in Table 3, in the columns labeled "Correlation W/Platelets". The "p" column shows the p-values for correlations with Platelets. A biomarker was selected on the basis of a marginal p-value for the Pearson product-moment correlation coefficient. In the example, p<0.01 was required for selection. The "p<cv" column indicates, by the presence of the word "YES," those biomarkers that became Candidate Biomarkers as a result of a "significant" correlation with Platelets.

Step 6. Fit a logistic regression model for each Potential Biomarker, using a binary indicator variable for the specified biological condition as the dependent (Y) variable and age and the Potential Biomarker as the independent (X) variables. Add to the list of Candidate Biomarkers each Potential Biomarker that is "statistically significant" in its logistic regression model.

A logistic regression model was fitted for each biomarker, using Disease Status as the dependent (Y) variable and a combination of age and the biomarker as the independent (X) variables. In this case, for each biomarker the logistic model assessed how well the probability of a hospitalization for a painful crisis is described by that biomarker, in conjunction with the subject's age. Roughly speaking, the biomarker's regression coefficient, or slope, in the logistic regression will be approximately zero if there is no relationship between the biomarker and the probability that the subject will acquire the specified biological condition; a nonzero slope indicates a relationship. A summary of the logistic regression results is shown in Table 3, in the columns headed "Logistic Regression." The "p" column shows the p-values for the biomarker's regression coefficient. A biomarker was selected on the basis of a marginal p-value for the biomarker's slope in the logistic regression model. In the example, p<0.01 was required for selection. The "p<cv" column indicates, by the presence of the word "YES," those biomarkers that became Candidate Biomarkers as a result of a "significant" logistic regression coefficient. Note that some of these biomarkers were also significantly correlated with Platelets and were Candidate Biomarkers before the logistic regressions were computed.

Step 7: Evaluate each longitudinally-assessed Potential Biomarker, using a general linear mixed model ("MixMod") to assess whether longitudinal trends in the biomarker's values are related to acquisition of the specified biological condition. Each Potential Biomarker with a statistically significant longitudinal trend is moved to the list of Candidate Biomarkers.

A mixed model was fitted for each biomarker, using longitudinal values of the biomarker as the dependent (Y) variable, with Age, Disease Status, and Visit Number× Disease Status as the independent (X) variables, and a subject effect in the random effects (Z) part of the model. (Visit Number and Disease Status are "classification" variables; the corresponding coefficients are increments to an intercept. In contrast, Age is a continuous variable whose coefficient is a slope.) The random effects part of the mixed model incorporates the correlations between longitudinal measurements from the same subject. The model permits the number of visits (longitudinal assessments) to vary from subject to subject.

A biomarker could be selected if either the Disease Status "main effect" or the subvector of three Visit Number× Disease Status interaction coefficients was statistically significantly different from zero (p<0.01). A significant Disease Status "main effect" would indicate that the mean of the biomarker values for subjects in Group D is different from the mean for subjects in Group $\overline{D}$. A significant subvector of three Visit Number×Disease Status interaction coefficients would indicate that the time trend in biomarker values for subjects in Group D is different than time trend for subjects in Group $\overline{D}$. In either case (significant main effect or interaction), the results would indicate that the biomarker is a potentially useful discriminator and should be moved to the Candidate Biomarker list. The results from the mixed models are shown in Table 3 in the columns headed Mixed Model. Separate results are shown for main effects and interactions, in a format similar to results from correlations and logistic regressions.

At the end of Steps 4–7, all Potential Biomarkers have been examined and each biomarker with historical or quantitative evidence of utility as a discriminator has been moved to the list of Candidate Biomarkers. The Candidate Biomarkers are indicated by the word "YES" in Table 3 in the column headed "Selected."

Phase II. Reduce the Candidate Biomarkers to a Set of Select Biomarkers that have Discriminatory Power and Perform Mixed Model Estimation of the Covariance Structure and Predicted Values Step 1. Prepare a dataset in which one variable, "RespScal," contains scaled values (including longitudinal measures) of all Candidate Biomarkers from all subjects.

This step was executed for the example but the results are not shown. However, note that when all the values of all the different biomarkers are placed into one column vector, Y, the vector can contain a large number of elements.

Step 2. Fit a general linear mixed model (MixMod) using the specifications listed below, obtain estimates of the parameter matrices $\beta$, $\Delta$, and V, obtain estimates of each subject's random subject effects, $d_{ik}$, and each subject's "predicted values," $Y_{ik}^{(min)}$ and $Y_{ik}^{(avg)}$ as if the subject were in each specified biological condition group, i=1, 2.

Step 3: Delete the biomarker that has the least apparent discriminant power and re-fit the mixed model.

Steps 2–3 are repeated iteratively until all biomarkers in the model are statistically significant. In the interests of conserving space in this presentation of an example, only the final results of the iterations through Steps 2–3 are discussed. Steps 2–3 reduced the number of biomarkers to 15, with Age as a fixed effect covariate.

General information for the example mixed model is given in Table 4. Data were available from 481 patients with a maximum of three visits for each patient. Note the apparently large numbers of observations not used in the analysis. Artificial observations were generated with missing Y values to compel the software to compute the required predicted values. The artificial observations with missing Y values have no impact on the estimation of parameters or prediction of random subject effects.

Table 5 gives the estimates of the fixed effects from the mixed model. The p-value for each biomarker (e.g., the p-value for "L_BUN") is a p-value for a test of the hypothesis that the mean value of this biomarker is the same as the overall mean, averaged over all biomarkers. The fact that these p-values are significant is of little interest; one expects the mean of one biomarker's values to be different from the mean of another biomarker's values.

In Table 5 the p-value for each "biomarker X GROUP IA" interaction (e.g., the p-value for "ALBUMIN X GROUP IA") is a p-value for a test of the hypothesis that the mean value of the biomarker for Group D is significantly different from the mean value of the biomarker for Group $\overline{D}$. A significant value (e.g., p<0.05) indicates that the biomarker should be a good discriminator. All of the interactions in the final model represented by Table 5 are statistically significant (all p≦0.05). Age was forced to remain in the model even though the p-value is not significant.

Subject-, biomarker-, Disease Status ("Group")-, and visit-specific observed and predicted values for subject 447 are shown in Table 6. This subject was in Group $\overline{D}$ ("GROUP D?"=NO; note "RESPSCAL" is missing for rows with "GROUP D?"=YES), but we have Predicted values for both groups. Note also that this subject had no data for biomarker MCH or MCHC for Visit 2, but we have model-based predicted values for that subject's Visit 2 MCH and MCHC.

The strategy implemented in Steps 2–3 is an analog of a "backwards elimination" procedure in the stepwise regression context. An alternative would be to implement an analog of "forward selection," in which one initially includes only two (or very small numbers of) clearly effective discriminants (biomarkers) in the model and, at each subsequent step, adds one more biomarker.

Step) 4: Determine the structures of the covariance parameter matrices, $\Delta_i$, and $V_{ik}$.

As noted above, the overall structure of $\Sigma_{ik}$ must take into account three types of covariances/correlations:

Type ADB: Covariances/correlations among different biomarkers evaluated at the same time point;

Type ALESB: Covariances/correlations among longitudinal evaluations of a single biomarker;

Type BTBEL: Covariances/correlations between two biomarkers, evaluated longitudinally, i.e., covariances/correlations between any pair of biomarkers, one evaluated at one time and the other evaluated at a different time.

In the example the following structures were ultimately obtained:

Identical random effects covariance parameter matrices for both Group D and Group $\overline{D}$, i.e., $\Delta_1 = \Delta_2 = \Delta$ and $\Delta$ has compound symmetric structure, $\delta_{ii} = 0.6669$, $\delta_{ij} = 0.0097$ for i≠j.

Type ADB covariances in matrix V, which is the same for both Group D and Group $\overline{D}$, and compound symmetric structure, $v_{ii} = 0.3267$, $v_{ij} = 0.0151$ for i≠j.

This covariance structure was reasonable given the sickle cell data at hand.

Estimates of $\Delta$ and V are shown in Table 7. The estimate of $\Delta$, the covariance matrix of the random subject effects, is in the top of the table. The rows and columns correspond to the 15 biomarkers used in this model; the columns are labeled.

The estimate of V, the covariance matrix of the within-subject, within-visit errors, is in the bottom of the table. As with $\Delta$, the rows and columns correspond to the 15 biomarkers used in this model. V has compound symmetric structure, which is reasonable for the scaled data.

Phase III: Calculate Discriminant Functions Using Estimated Means and Predicted Values and Compute Logistic Predicted Values for each Subject; Estimate Error Rates for the Discriminant Functions Step 1. Using results from the Phase II mixed model, classify all subjects in the validation sample and estimate the error rates of multiple candidate discriminant procedures, one based on "estimated values," and others based upon "predicted values" utilizing various combinations of the estimated random subject effects. The procedure with the lowest estimated error rate is selected procedure and is referred to as the "apparently most reliable procedure."

The present procedures were applied using the mixed model results for the sickle cell data. Since the covariance parameter matrices were modeled to be equal for Group D and Group $\overline{D}$, each discriminant was a linear discriminant. Each discriminant was applied to the subjects in the training sample (used here as a validation sample), projecting each subject to belong to either Group PD or Group $\overline{PD}$.

An evaluation of the subject linear discriminant function based on estimated values is shown in Table 8. Of 179 subjects in Group $\overline{D}$, the Disease Status="No" group, 100 (56%) were correctly classified by the discriminant into Group $\overline{PD}$ and 79 (448%) were incorrectly classified into Group PD. Of 262 subjects in Group D, the Disease Status= "Yes" group, 188 (72%) were correctly classified into Group PD and 74 (28%) were incorrectly classified into Group $\overline{PD}$. Overall, of 441 subjects, 288 subjects (65%) were correctly classified and 35% were misclassified.

Table 9 displays an evaluation of the subject linear discriminant function based on predicted values using the minimum random subject effect. Table 9 is similar to Table 8. Prediction discrimination led to a slight improvement of discrimination in Group $\overline{D}$, but slightly worse results in Group D. Overall, the error rate was approximately the same.

The classification/misclassification statistics in the preceding paragraph and in Tables 8–9 are optimistically biased, that is, the table provides a more favorable estimate of misclassification rates than are likely to occur in practice, because the training sample was used both to derive the discriminant function and to evaluate it. Evaluation of the discriminant function using the evaluation sample will produce unbiased estimates of the misclassification rates. Resampling techniques such as jackknifing or bootstrapping can produce less biased estimates while still using data from the training sample.

Step 2. Use two types of logistic regression to complete estimates of the probability that a new subject will belong to each group.

Two types of logistic regressions are fitted to the training sample data for each of the discriminant functions. In both logistic regressions, the Disease Status indicator is the dependent ("Y") variable. In the first logistic regression, the value of the discriminant functions based on estimation is used as an independent ("X") variable. In the second logistic regression, the value of the discriminant functions based on prediction is used as an independent ("X") variable. In a third logistic regression, the biomarkers used in the discriminant function are incorporated as independent ("X") variables, along with covariates used in the fixed effects part of the mixed model, and the Disease Status indicator is the dependent ("Y") variable. The estimates from the logistic regression models are used to compute, for each subject, an estimated probability that the subject belongs to the diseased (Disease Status "Yes") group. The results of the logistic regression computations are not displayed in tables.

FIG. 1 displays the empirical distribution functions ("EDF") of the linear discriminant function values (based on estimated values) for Group D (solid line) and Group $\overline{D}$ (dashed line). To prepare the graph, the data for the subjects are sorted by Disease Status group and, within a group, by increasing values of D(Y). Data points are plotted in that sequence. The EDF value starts at 0 (before the first subject's data are plotted) and increases by 1/n for each subject, where n is the number of subjects in that group. Thus, the EDF climbs from 0 to 1, separately for each group. In FIG. 1, the fact that the EDF for Group D is shifted to the left of the EDF for Group $\overline{D}$ indicates that Group D tends to have lower scores than Group $\overline{D}$.

One can see that roughly 72% of Group D subjects have D(Y) values less than 0 (the separation point between Group PD and Group $\overline{PD}$), while Group $\overline{D}$ has about 44% of their subjects' EDF values to the left of 0. The steepness of the groups' EDF lines near the vertical line at LDF=0 indicates that many subjects are "borderline" and are difficult to classify. It is possible that if an additional year of followup had been available, a number of subjects in Group $\overline{D}$ (in these data) would have had pain crises in the subsequent year and would have "converted" to Group D.

Figure 2:
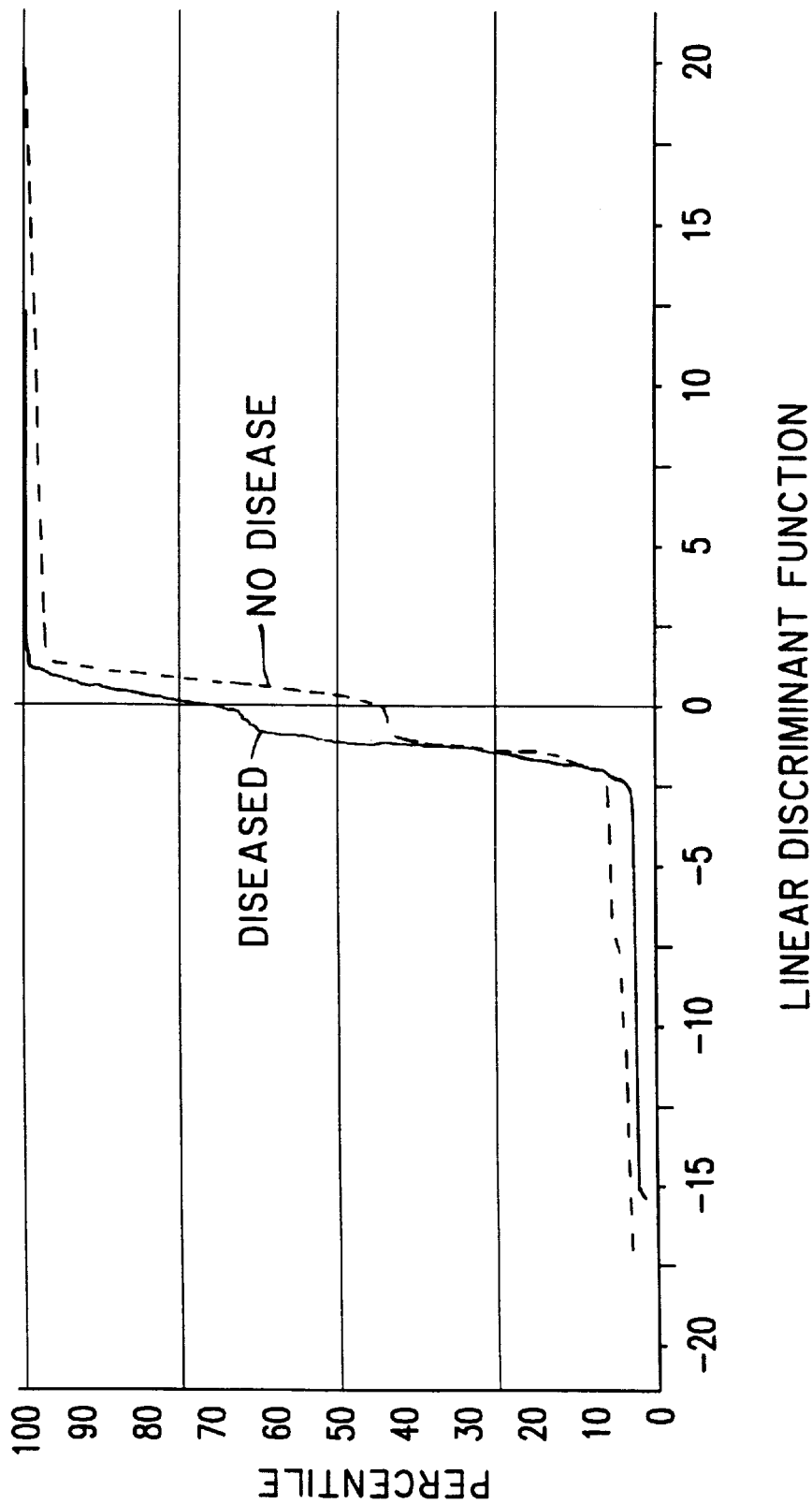
FIG. 2 shows the empirical distribution functions ("EDF") of the linear discriminant function values, based on minimum random subject effect predicted values for Group D and Group $\overline{D}$ of the Example.

The empirical distribution functions ("EDF") of the minimum random subject linear discriminant function values for Group D (solid line) and Group $\overline{D}$ (dashed line) are shown in FIG. 2. The results and interpretations are similar to those in FIG. 1. However, the group's EDF lines are even steeper, in the vicinity of LDF=0, in FIG. 2 than in FIG. 1, emphasizing the fact that many subjects are borderline.

These Figures reveal, as do the statistics above, that the discriminant procedures effectively classifies subjects who ultimately must be hospitalized for a pain crisis but, for the limited data available in this example, the procedures are less effective for the subgroup who will not be so hospitalized.

TABLE 2

Description of Potential Biomarkers for the Sickle Cell Data

| Variable Name | Description |
| --- | --- |
| AGEYR | Age of patient (years) |
| ALBUMIN | Albumin (g/dL) |
| ALKPHOS | Alkaline Phosphatase (u/L) |
| BMI | Body Mass Index (Wt./Ht.2) |
| BP_DIAST | Diastolic Blood Pressure (mm Hg) |
| BP_SYST | Systolic Blood Pressure (mm Hg) |
| CALCIUM | Calcium (g/dL) |
| CL | Chloride (meq/L) |
| CO2 | Carbon Dioxide (mmol/L) |
| GENDER | Gender of patient (M/F) |
| HBA2 | Hemoglobin A2 (%) |
| HCT | Hematocrit (%) |
| HEIGHT | Height (cm) |
| HGB | Hemoglobin (g/dl) |
| K | Potassium (mmol/L) |
| L_ALKPH | Log 10 of Alkaline Phosphatase |
| L_ALT | Log 10 of Alanine Transaminase |
| L_AST | Log 10 of Aspartate Transaminase |
| L_BUN | Log 10 of Blood Urea Nitrogen |
| L_CR | Log 10 of Creatinine |
| L_DBILI | Log 10 of Direct Bilirubin |
| L_HBF | Log 10 of Hemoglobin F |
| L_LDH | Log 10 of Lactic Dehydrogenase |
| L_TBILI | Log 10 of Total Bilirubin |
| L_URICA | Log 10 of Uric Acid |
| MCH | Mean Corpuscular Hemoglobin (mg/dL) |
| MCHC | Mean Corpuscular Hemoglobin Concentration (b/dL) |
| MCV | Mean Corpuscular Volume (fl) |
| NA | Sodium (meq/L) |
| PHOSPHOR | Phosphorus (mg/dL) |
| PLATELET | Platelet Count (×109/L) |
| RBC | Red Blood Cell Count (×109/L) |
| RETIC | Reticulocyte Count (%) |
| TOTPROT | Total Blood Protein (g/L) |
| WBC | White Blood Cell Count (×109/L) |
| WEIGHT | Weight of patient (kg) |

TABLE 3

Summary of Phase I, Steps 5–7, the Selection of Candidate Biomarkers from a List of Potential Biomarkers using Correlation, Logistic Regression, and Mixed Models.

| Variable | Se-lected | Group D (Afflicted) | | | Group D-Bar (Not Afflicted) | | | Correlation W/Platelets | | Mixed Model | | | | Logistic Regression | |
| --- | --- | --- | --- | --- | --- | --- | --- | --- | --- | --- | --- | --- | --- | --- | --- |
| | | Numbers of Subjects | Mean Obs'ns | Std. Dev. | Numbers of Subjects | Mean Obs'ns | Std. Dev. | p | p < cv | Main Effect p | p < cv | Interactions p | p < cv | p | p < cv |
| AGEYR | | 294 | 353 | 20.99 | 14.42 | 187 | 288 | 17.74 | 15.59 | NA | | NA | | NA | | NA |
| ALBUMIN | | 231 | 278 | 4.31 | 0.47 | 160 | 251 | 4.43 | 0.39 | 0.28 | | 0.02 | | 0.83 | | 0.01 |
| ALKPHOS | | 233 | 280 | 159.00 | 86.80 | 160 | 251 | 169.14 | 112.96 | 0.43 | | 0.47 | | 0.71 | | 0.57 |
| BMI | | 225 | 275 | 0.00 | 0.00 | 164 | 252 | 0.00 | 0.00 | 0.08 | | 0.18 | | 0.53 | | 0.38 |
| BP_DIAST | YES | 258 | 310 | 61.80 | 12.26 | 168 | 251 | 62.17 | 13.28 | 0.00 | YES | 0.21 | | 0.41 | | 0.36 |
| BP_SYST | | 258 | 310 | 111.29 | 16.54 | 168 | 251 | 110.15 | 19.18 | 0.98 | | 0.99 | | 0.06 | | 0.97 |
| CALCIUM | | 236 | 283 | 9.27 | 0.52 | 159 | 250 | 9.41 | 0.51 | 0.03 | | 0.01 | | 0.24 | | 0.03 |
| Cl | | 246 | 291 | 104.90 | 3.61 | 157 | 242 | 104.73 | 3.59 | 0.73 | | 0.63 | | 0.32 | | 0.31 |

TABLE 3-continued

Summary of Phase I, Steps 5–7, the Selection of Candidate Biomarkers from a List of Potential Biomarkers using Correlation, Logistic Regression, and Mixed Models.

| | | Group D (Afflicted) | | | Group D-Bar (Not Afflicted) | | | Correlation W/Platelets | | Mixed Model Main Effect | | Mixed Model Interactions | | Logistic Regression | |
|---|---|---|---|---|---|---|---|---|---|---|---|---|---|---|---|
| Variable | Se-lected | Numbers of Subjects | Mean Obs'ns | Std. Dev. | Numbers of Subjects | Mean Obs'ns | Std. Dev. | p | p < cv | p | p < cv | p | p < cv | p | p < cv |
| CO2 | YES | 246 | 291 | 24.30 | 3.10 | 158 | 243 | 24.74 | 3.07 | 0.00 | YES | 0.05 | | 0.38 | | 0.13 | |
| GENDER | | 286 | 345 | 0.48 | 0.50 | 183 | 283 | 0.51 | 0.50 | 0.29 | | 0.90 | | 0.08 | | 0.88 | |
| HBA2 | | 76 | 91 | 2.99 | 0.81 | 40 | 63 | 3.14 | 1.05 | 0.17 | | 0.26 | | 0.46 | | 0.05 | |
| HCT | YES | 204 | 254 | 26.98 | 5.67 | 168 | 263 | 28.03 | 6.37 | 0.00 | YES | 0.02 | | 0.45 | | 0.01 | |
| HEIGHT | | 227 | 277 | 142.16 | 32.82 | 165 | 254 | 138.63 | 27.95 | 0.93 | | 0.63 | | 0.44 | | 0.50 | |
| HGB | YES | 203 | 253 | 9.02 | 1.89 | 168 | 263 | 9.53 | 2.08 | 0.00 | YES | 0.00 | YES | 0.46 | | 0.00 | YES |
| K | YES | 246 | 291 | 4.33 | 0.50 | 157 | 243 | 4.34 | 0.48 | 0.00 | YES | 0.81 | | 0.38 | | 0.46 | |
| L_ALKPH | | 233 | 280 | 2.15 | 0.20 | 160 | 251 | 2.16 | 0.24 | 0.82 | | 0.51 | | 0.35 | | 0.55 | |
| L_ALT | YES | 228 | 273 | 1.38 | 0.30 | 153 | 242 | 1.32 | 0.22 | 0.13 | | 0.00 | YES | 0.86 | | 0.00 | YES |
| L_AST | YES | 240 | 287 | 1.68 | 0.25 | 161 | 254 | 1.63 | 0.20 | 0.00 | YES | 0.00 | YES | 0.76 | | 0.00 | YES |
| L_BUN | YES | 223 | 261 | 0.83 | 0.23 | 147 | 222 | 0.89 | 0.20 | 0.00 | YES | 0.00 | YES | 0.25 | | 0.00 | YES |
| L_CR | | 250 | 298 | −0.24 | 0.27 | 159 | 252 | −0.32 | 0.27 | 0.08 | | 0.12 | | 0.21 | | 0.06 | |
| L_DBILI | | 51 | 53 | −0.38 | 0.30 | 29 | 35 | −0.48 | 0.23 | 0.72 | | 0.10 | | 0.58 | | 0.10 | |
| L_HBF | | 95 | 113 | 0.83 | 0.45 | 80 | 118 | 0.75 | 0.45 | 0.84 | | 0.11 | | 0.32 | | 0.08 | |
| L_LDH | | 136 | 158 | 2.59 | 0.32 | 96 | 142 | 2.58 | 0.24 | 0.02 | | 0.46 | | 0.48 | | 0.63 | |
| L_TBILI | YES | 234 | 280 | 0.33 | 0.31 | 159 | 252 | 0.31 | 0.31 | 0.00 | YES | 0.11 | | 0.48 | | 0.09 | |
| L_URICA | | 231 | 278 | 0.69 | 0.15 | 158 | 250 | 0.70 | 0.15 | 0.83 | | 0.04 | | 0.63 | | 0.25 | |
| MCH | YES | 162 | 195 | 29.10 | 4.03 | 145 | 219 | 28.22 | 4.00 | 0.00 | YES | 0.20 | | 0.43 | | 0.13 | |
| MCHC | YES | 168 | 205 | 33.59 | 1.30 | 150 | 226 | 34.19 | 1.60 | 0.91 | | 0.00 | YES | 0.62 | | 0.01 | YES |
| MCV | YES | 203 | 250 | 87.29 | 11.67 | 166 | 259 | 82.72 | 11.31 | 0.00 | YES | 0.00 | YES | 0.35 | | 0.00 | YES |
| NA | | 246 | 291 | 140.16 | 2.76 | 157 | 243 | 140.27 | 2.32 | 0.09 | | 0.47 | | 0.14 | | 0.86 | |
| PHOSPHOR | YES | 214 | 257 | 4.18 | 0.82 | 151 | 236 | 4.44 | 0.87 | 0.01 | YES | 0.04 | | 0.57 | | 0.04 | |
| PLATELET | YES | 199 | 248 | 419.49 | 183.43 | 168 | 263 | 355.79 | 146.53 | 1.00 | | 0.00 | YES | 0.95 | | 0.00 | YES |
| RBC | YES | 202 | 250 | 3.18 | 0.92 | 165 | 259 | 3.48 | 1.01 | 0.00 | YES | 0.00 | YES | 0.18 | | 0.00 | YES |
| RETIC | YES | 92 | 115 | 8.16 | 5.64 | 86 | 130 | 6.45 | 4.91 | 0.00 | YES | 0.01 | YES | 0.56 | | 0.01 | YES |
| TOTPROT | YES | 232 | 279 | 7.65 | 0.71 | 159 | 251 | 7.60 | 0.60 | 0.00 | YES | 0.41 | | 0.16 | | 0.96 | |
| WBC | YES | 202 | 251 | 11.91 | 4.54 | 168 | 263 | 10.27 | 4.14 | 0.00 | YES | 0.00 | YES | 0.92 | | 0.00 | YES |
| WEIGHT | | 263 | 316 | 49.44 | 27.97 | 175 | 269 | 44.04 | 28.43 | 0.14 | | 0.52 | | 0.75 | | 0.30 | |

NOTES for Table 2:
"p < cv" is an abbreviation for "The p-value is less than the critical value; here, cv = 0.01.
In "p < cv" columns, a blank means "NO."
All p-values have been rounded to 2 decimal places.

TABLE 4

Mixed Model Information: Overall Model Characteristics

| | |
|---|---|
| Covariance Parameters | 4 |
| Columns in X | 31 |
| Max Cols in Z Per Subject | 15 |
| Subjects | 481 |
| Max Obs Per Subject | 90 |
| Observations Used | 7254 |
| Observations Not Used | 11946 |
| Total Observations | 19200 |

TABLE 5

Estimates of Fixed Effects Coefficients and Related Statistics

| Biomarker Main Effect or Interaction (IA) | $\hat{\beta}$ | s.e.($\hat{\beta}$) | t | p-Value |
|---|---|---|---|---|
| ALBUMIN | 10.067 | 0.073 | 137.03 | 0.0000 |
| CALCIUM | 18.155 | 0.074 | 246.45 | 0.0000 |
| HCT | 4.632 | 0.072 | 64.08 | 0.0000 |
| HGB | 4.699 | 0.072 | 65.01 | 0.0000 |
| L_ALT | 4.964 | 0.074 | 66.70 | 0.0000 |
| L_AST | 7.154 | 0.073 | 97.74 | 0.0000 |
| L_BUN | 4.124 | 0.077 | 53.78 | 0.0000 |
| MCH | 6.949 | 0.077 | 90.19 | 0.0000 |
| MCHC | 22.567 | 0.076 | 296.69 | 0.0000 |
| MCV | 7.067 | 0.073 | 97.21 | 0.0000 |
| PHOSPHOR | 4.912 | 0.075 | 65.17 | 0.0000 |
| PLATELET | 2.166 | 0.072 | 29.97 | 0.0000 |
| RBC | 3.335 | 0.073 | 45.97 | 0.0000 |
| RETIC | 1.164 | 0.099 | 11.79 | 0.0000 |
| WBC | 2.335 | 0.072 | 32.31 | 0.0000 |
| ALBUMIN X GROUP IA | −0.303 | 0.098 | −3.11 | 0.0019 |
| CALCIUM X GROUP IA | −0.374 | 0.097 | −3.84 | 0.0001 |
| HCT X GROUP IA | −0.195 | 0.099 | −1.97 | 0.0489 |
| HGB X GROUP IA | −0.270 | 0.099 | −2.73 | 0.0064 |
| L_ALT X GROUP IA | 0.286 | 0.098 | 2.91 | 0.0036 |
| L_AST X GROUP IA | 0.298 | 0.096 | 3.08 | 0.0020 |
| L_BUN X GROUP IA | −0.290 | 0.101 | −2.87 | 0.0041 |
| MCH X GROUP IA | 0.225 | 0.108 | 2.08 | 0.0377 |
| MCHC X GROUP IA | −0.322 | 0.107 | −3.02 | 0.0025 |
| MCV X GROUP IA | 0.390 | 0.099 | 3.92 | 0.0001 |
| PHOSPHOR X GROUP IA | −0.335 | 0.101 | −3.33 | 0.0009 |
| PLATELET X GROUP IA | 0.320 | 0.099 | 3.21 | 0.0013 |
| RBC X GROUP IA | −0.337 | 0.099 | −3.39 | 0.0007 |
| RETIC X GROUP IA | 0.390 | 0.142 | 2.75 | 0.0059 |
| WBC X GROUP IA | 0.367 | 0.099 | 3.70 | 0.0002 |
| AGE (CENTERED) | −0.001 | 0.001 | −0.87 | 0.3848 |

TABLE 6

Predicted Values and Related Statistics for Subject 447

| ID | BIOMARKR | VISIT | GROUP D? | RESPSCAL | TYPE OF RECORD | PREDMEAN | PRED |
|---|---|---|---|---|---|---|---|
| 447 | ALBUMIN | 1 | NO | 9.998 | REAL | 10.049 | 9.990 |
| 447 | ALBUMIN | 2 | NO | 9.998 | REAL | 10.048 | 9.989 |
| 447 | ALBUMIN | 3 | NO | 9.998 | REAL | 10.047 | 9.988 |
| 447 | CALCIUM | 1 | NO | 17.883 | REAL | 18.137 | 17.681 |
| 447 | CALCIUM | 2 | NO | 16.922 | REAL | 18.136 | 17.681 |
| 447 | CALCIUM | 3 | NO | 18.076 | REAL | 18.135 | 17.680 |
| 447 | HCT | 1 | NO | 6.737 | REAL | 4.613 | 6.513 |
| 447 | HCT | 2 | NO | 6.853 | REAL | 4.613 | 6.512 |
| 447 | HCT | 3 | NO | 6.903 | REAL | 4.612 | 6.511 |
| 447 | HGB | 1 | NO | 6.712 | REAL | 4.680 | 6.590 |
| 447 | HGB | 2 | NO | 6.909 | REAL | 4.679 | 6.589 |
| 447 | HGB | 3 | NO | 7.107 | REAL | 4.678 | 6.588 |
| 447 | L_ALT | 1 | NO | 5.623 | REAL | 4.945 | 5.218 |
| 447 | L_ALT | 2 | NO | 5.675 | REAL | 4.945 | 5.217 |
| 447 | L_ALT | 3 | NO | 4.540 | REAL | 4.944 | 5.217 |
| 447 | L_AST | 1 | NO | 6.960 | REAL | 7.136 | 7.293 |
| 447 | L_AST | 2 | NO | 7.897 | REAL | 7.135 | 7.293 |
| 447 | L_AST | 3 | NO | 7.151 | REAL | 7.134 | 7.292 |
| 447 | L_BUN | 1 | NO | 3.606 | REAL | 4.106 | 4.060 |
| 447 | L_BUN | 2 | NO | 4.185 | REAL | 4.105 | 4.060 |
| 447 | L_BUN | 3 | NO | 4.422 | REAL | 4.104 | 4.059 |
| 447 | MCH | 1 | NO | 7.156 | REAL | 6.931 | 7.147 |
| 447 | MCH | 2 | NO | | REAL | 6.930 | 7.146 |
| 447 | MCH | 3 | NO | 7.279 | REAL | 6.929 | 7.145 |
| 447 | MCHC | 1 | NO | 21.994 | REAL | 22.549 | 22.191 |
| 447 | MCHC | 2 | NO | | REAL | 22.548 | 22.191 |
| 447 | MCHC | 3 | NO | 22.259 | REAL | 22.547 | 22.190 |
| 447 | MCV | 1 | NO | 7.438 | REAL | 7.048 | 7.399 |
| 447 | MCV | 2 | NO | 7.378 | REAL | 7.047 | 7.398 |
| 447 | MCV | 3 | NO | 7.600 | REAL | 7.046 | 7.397 |
| 447 | PHOSPHOR | 1 | NO | 3.180 | REAL | 4.894 | 3.620 |
| 447 | PHOSPHOR | 2 | NO | 3.399 | REAL | 4.893 | 3.619 |
| 447 | PHOSPHOR | 3 | NO | 3.728 | REAL | 4.892 | 3.618 |
| 447 | PLATELET | 1 | NO | 2.335 | REAL | 2.148 | 2.267 |
| 447 | PLATELET | 2 | NO | 2.501 | REAL | 2.147 | 2.266 |
| 447 | PLATELET | 3 | NO | 2.073 | REAL | 2.146 | 2.265 |
| 447 | RBC | 1 | NO | 4.688 | REAL | 3.316 | 4.511 |
| 447 | RBC | 2 | NO | 4.593 | REAL | 3.315 | 4.510 |
| 447 | RBC | 3 | NO | 4.871 | REAL | 3.314 | 4.509 |
| 447 | RETIC | 1 | NO | | REAL | 1.145 | 1.197 |
| 447 | RETIC | 2 | NO | | REAL | 1.145 | 1.196 |
| 447 | RETIC | 3 | NO | | REAL | 1.144 | 1.195 |
| 447 | WBC | 1 | NO | 3.069 | REAL | 2.317 | 2.561 |
| 447 | WBC | 2 | NO | 1.873 | REAL | 2.316 | 2.561 |
| 447 | WBC | 3 | NO | 2.911 | REAL | 2.315 | 2.560 |
| 447 | ALBUMIN | 1 | YES | | UNREAL | 10.049 | 9.990 |
| 447 | ALBUMIN | 2 | YES | | UNREAL | 10.048 | 9.989 |
| 447 | ALBUMIN | 3 | YES | | UNREAL | 10.047 | 9.988 |
| 447 | CALCIUM | 1 | YES | | UNREAL | 18.137 | 17.681 |
| 447 | CALCIUM | 2 | YES | | UNREAL | 18.136 | 17.681 |
| 447 | CALCIUM | 3 | YES | | UNREAL | 18.135 | 17.680 |
| 447 | HCT | 1 | YES | | UNREAL | 4.613 | 6.513 |
| 447 | HCT | 2 | YES | | UNREAL | 4.613 | 6.512 |
| 447 | HCT | 3 | YES | | UNREAL | 4.612 | 6.511 |
| 447 | HGB | 1 | YES | | UNREAL | 4.680 | 6.590 |
| 447 | HGB | 2 | YES | | UNREAL | 4.679 | 6.589 |
| 447 | HGB | 3 | YES | | UNREAL | 4.678 | 6.588 |
| 447 | L_ALT | 1 | YES | | UNREAL | 4.945 | 5.218 |
| 447 | L_ALT | 2 | YES | | UNREAL | 4.945 | 5.217 |
| 447 | L_ALT | 3 | YES | | UNREAL | 4.944 | 5.217 |
| 447 | L_AST | 1 | YES | | UNREAL | 7.136 | 7.293 |
| 447 | L_AST | 2 | YES | | UNREAL | 7.135 | 7.293 |
| 447 | L_AST | 3 | YES | | UNREAL | 7.134 | 7.292 |
| 447 | L_BUN | 1 | YES | | UNREAL | 4.106 | 4.060 |
| 447 | L_BUN | 2 | YES | | UNREAL | 4.105 | 4.060 |
| 447 | L_BUN | 3 | YES | | UNREAL | 4.104 | 4.059 |
| 447 | MCH | 1 | YES | | UNREAL | 6.931 | 7.147 |
| 447 | MCH | 2 | YES | | UNREAL | 6.930 | 7.146 |
| 447 | MCH | 3 | YES | | UNREAL | 6.929 | 7.145 |
| 447 | MCHC | 1 | YES | | UNREAL | 22.549 | 22.191 |
| 447 | MCHC | 2 | YES | | UNREAL | 22.548 | 22.191 |
| 447 | MCHC | 3 | YES | | UNREAL | 22.547 | 22.190 |
| 447 | MCV | 1 | YES | | UNREAL | 7.048 | 7.399 |
| 447 | MCV | 2 | YES | | UNREAL | 7.047 | 7.398 |

TABLE 6-continued

Predicted Values and Related Statistics for Subject 447

| ID | BIOMARKR | VISIT | GROUP D? | RESPSCAL | TYPE OF RECORD | PREDMEAN | PRED |
|---|---|---|---|---|---|---|---|
| 447 | MCV | 3 | YES | | UNREAL | 7.046 | 7.397 |
| 447 | PHOSPHOR | 1 | YES | | UNREAL | 4.894 | 3.620 |
| 447 | PHOSPHOR | 2 | YES | | UNREAL | 4.893 | 3.619 |
| 447 | PHOSPHOR | 3 | YES | | UNREAL | 4.892 | 3.618 |
| 447 | PLATELET | 1 | YES | | UNREAL | 2.148 | 2.267 |
| 447 | PLATELET | 2 | YES | | UNREAL | 2.147 | 2.266 |
| 447 | PLATELET | 3 | YES | | UNREAL | 2.146 | 2.265 |
| 447 | RBC | 1 | YES | | UNREAL | 3.316 | 4.511 |
| 447 | RBC | 2 | YES | | UNREAL | 3.315 | 4.510 |
| 447 | RBC | 3 | YES | | UNREAL | 3.314 | 4.509 |
| 447 | RETIC | 1 | YES | | UNREAL | 1.145 | 1.197 |
| 447 | RETIC | 2 | YES | | UNREAL | 1.145 | 1.196 |
| 447 | RETIC | 3 | YES | | UNREAL | 1.144 | 1.195 |
| 447 | WBC | 1 | YES | | UNREAL | 2.317 | 2.561 |
| 447 | WBC | 2 | YES | | UNREAL | 2.316 | 2.561 |
| 447 | WBC | 3 | YES | | UNREAL | 2.315 | 2.560 |

TABLE 7

Estimates of Covariance Matrices from Proc Mixed

| Biomarker Variables | ALBUMIN | CALCIUM | HCT | HGB | L_ALT | L_AST | L_BUN | MCH | MCHC | MCV | PHOSPHOR | PLATELET | RBC | RETIC | WBC |
|---|---|---|---|---|---|---|---|---|---|---|---|---|---|---|---|
| Estimated Covariance Matrix of Random Effects, $\hat{\Delta}$ |||||||||||||||| 
| ALBUMIN | 0.6669 | 0.0097 | 0.0097 | 0.0097 | 0.0097 | 0.0097 | 0.0097 | 0.0097 | 0.0097 | 0.0097 | 0.0097 | 0.0097 | 0.0097 | 0.0097 | 0.0097 |
| CALCIUM | 0.0097 | 0.6669 | 0.0097 | 0.0097 | 0.0097 | 0.0097 | 0.0097 | 0.0097 | 0.0097 | 0.0097 | 0.0097 | 0.0097 | 0.0097 | 0.0097 | 0.0097 |
| HCT | 0.0097 | 0.0097 | 0.6669 | 0.6669 | 0.0097 | 0.0097 | 0.0097 | 0.0097 | 0.0097 | 0.0097 | 0.0097 | 0.0097 | 0.0097 | 0.0097 | 0.0097 |
| HGB | 0.0097 | 0.0097 | 0.6669 | 0.6669 | 0.0097 | 0.0097 | 0.0097 | 0.0097 | 0.0097 | 0.0097 | 0.0097 | 0.0097 | 0.0097 | 0.0097 | 0.0097 |
| L_ALT | 0.0097 | 0.0097 | 0.0097 | 0.0097 | 0.6669 | 0.6669 | 0.0097 | 0.0097 | 0.0097 | 0.0097 | 0.0097 | 0.0097 | 0.0097 | 0.0097 | 0.0097 |
| L_AST | 0.0097 | 0.0097 | 0.0097 | 0.0097 | 0.6669 | 0.6669 | 0.0097 | 0.0097 | 0.0097 | 0.0097 | 0.0097 | 0.0097 | 0.0097 | 0.0097 | 0.0097 |
| L_BUN | 0.0097 | 0.0097 | 0.0097 | 0.0097 | 0.0097 | 0.0097 | 0.6669 | 0.0097 | 0.0097 | 0.0097 | 0.0097 | 0.0097 | 0.0097 | 0.0097 | 0.0097 |
| MCH | 0.0097 | 0.0097 | 0.0097 | 0.0097 | 0.0097 | 0.0097 | 0.0097 | 0.6669 | 0.6669 | 0.6669 | 0.0097 | 0.0097 | 0.0097 | 0.0097 | 0.0097 |
| MCHC | 0.0097 | 0.0097 | 0.0097 | 0.0097 | 0.0097 | 0.0097 | 0.0097 | 0.6669 | 0.6669 | 0.6669 | 0.0097 | 0.0097 | 0.0097 | 0.0097 | 0.0097 |
| MCV | 0.0097 | 0.0097 | 0.0097 | 0.0097 | 0.0097 | 0.0097 | 0.0097 | 0.6669 | 0.6669 | 0.6669 | 0.0097 | 0.0097 | 0.0097 | 0.0097 | 0.0097 |
| PHOSPHOR | 0.0097 | 0.0097 | 0.0097 | 0.0097 | 0.0097 | 0.0097 | 0.0097 | 0.0097 | 0.0097 | 0.0097 | 0.6669 | 0.6669 | 0.0097 | 0.0097 | 0.0097 |
| PLATELET | 0.0097 | 0.0097 | 0.0097 | 0.0097 | 0.0097 | 0.0097 | 0.0097 | 0.0097 | 0.0097 | 0.0097 | 0.6669 | 0.6669 | 0.0097 | 0.0097 | 0.0097 |
| RBC | 0.0097 | 0.0097 | 0.0097 | 0.0097 | 0.0097 | 0.0097 | 0.0097 | 0.0097 | 0.0097 | 0.0097 | 0.0097 | 0.0097 | 0.6669 | 0.6669 | 0.0097 |
| RETIC | 0.0097 | 0.0097 | 0.0097 | 0.0097 | 0.0097 | 0.0097 | 0.0097 | 0.0097 | 0.0097 | 0.0097 | 0.0097 | 0.0097 | 0.6669 | 0.6669 | 0.0097 |
| WBC | 0.0097 | 0.0097 | 0.0097 | 0.0097 | 0.0097 | 0.0097 | 0.0097 | 0.0097 | 0.0097 | 0.0097 | 0.0097 | 0.0097 | 0.0097 | 0.0097 | 0.6669 |
| Estimated Covariance Matrix of Random Error Terms, $\hat{V}$ |||||||||||||||| 
| ALBUMIN | 0.3267 | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 |
| CALCIUM | 0.0151 | 0.3267 | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 |
| HCT | 0.0151 | 0.0151 | 0.3267 | 0.0151 | 0.0151 | 0.0151 | 0.0151 | 0.0151 | 0.0151 | 0.0151 | 0.0151 | 0.0151 | 0.0151 | 0.0151 | 0.0151 |
| HGB | 0.0151 | 0.0151 | 0.0151 | 0.3267 | 0.0151 | 0.0151 | 0.0151 | 0.0151 | 0.0151 | 0.0151 | 0.0151 | 0.0151 | 0.0151 | 0.0151 | 0.0151 |
| L_ALT | 0.0151 | 0.0151 | 0.0151 | 0.0151 | 0.3267 | 0.0151 | 0.0151 | 0.0151 | 0.0151 | 0.0151 | 0.0151 | 0.0151 | 0.0151 | 0.0151 | 0.0151 |
| L_AST | 0.0151 | 0.0151 | 0.0151 | 0.0151 | 0.0151 | 0.3267 | 0.0151 | 0.0151 | 0.0151 | 0.0151 | 0.0151 | 0.0151 | 0.0151 | 0.0151 | 0.0151 |
| L_BUN | 0.0151 | 0.0151 | 0.0151 | 0.0151 | 0.0151 | 0.0151 | 0.3267 | 0.0151 | 0.0151 | 0.0151 | 0.0151 | 0.0151 | 0.0151 | 0.0151 | 0.0151 |
| MCH | 0.0151 | 0.0151 | 0.0151 | 0.0151 | 0.0151 | 0.0151 | 0.0151 | 0.3267 | 0.0151 | 0.0151 | 0.0151 | 0.0151 | 0.0151 | 0.0151 | 0.0151 |
| MCHC | 0.0151 | 0.0151 | 0.0151 | 0.0151 | 0.0151 | 0.0151 | 0.0151 | 0.0151 | 0.3267 | 0.0151 | 0.0151 | 0.0151 | 0.0151 | 0.0151 | 0.0151 |
| MCV | 0.0151 | 0.0151 | 0.0151 | 0.0151 | 0.0151 | 0.0151 | 0.0151 | 0.0151 | 0.0151 | 0.3267 | 0.0151 | 0.0151 | 0.0151 | 0.0151 | 0.0151 |
| PHOSPHOR | 0.0151 | 0.0151 | 0.0151 | 0.0151 | 0.0151 | 0.0151 | 0.0151 | 0.0151 | 0.011 | 0.0151 | 0.3267 | 0.0151 | 0.0151 | 0.0151 | 0.0151 |
| PLATELET | 0.0151 | 0.0151 | 0.0151 | 0.0151 | 0.0151 | 0.0151 | 0.0151 | 0.0151 | 0.0151 | 0.0151 | 0.0151 | 0.3267 | 0.0151 | 0.0151 | 0.0151 |
| RBC | 0.0151 | 0.0151 | 0.0151 | 0.0151 | 0.0151 | 0.0151 | 0.0151 | 0.0151 | 0.0151 | 0.0151 | 0.0151 | 0.0151 | 0.3267 | 0.0151 | 0.0151 |
| RETIC | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 | 0.3267 | 0.0151 |
| WBC | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 | 0.0151 | 0.3267 |

TABLE 8

Evaluation of the Discriminant Procedure Using Estimated Values

| Numbers of subjects in the validation sample tabulated by actual and classified membership in D. | | Subject was classified as a member of Group: | |
|---|---|---|---|
| | | $\overline{PD}$ No | PD Yes |
| Subject was actually a member of Group: | $\overline{D}$ No | $N_{11} = 100$<br>$r_{11} = 56\%$ | $N_{12} = 79$<br>$r_{12} = r_{FP} = 44\%$ |
| | D Yes | $N_{21} = 74$<br>$r_{21} = r_{FN} = 28\%$ | $N_{22} = 188$<br>$r_{22} = 72\%$ |

$r_{tot} = 153/441 = 35\%$

TABLE 9

Evaluation of the Discriminant Procedure Using Predicted Values

| Numbers of subjects in the validation sample tabulated by actual and classified membership in D. | | Subject was classified as a member of Group: | |
|---|---|---|---|
| | | $\overline{PD}$ No | PD Yes |
| Subject was actually a member of Group: | $\overline{D}$ No | $N_{11} = 105$<br>$r_{11} = 59\%$ | $N_{12} = 74$<br>$r_{12} = r_{FP} = 41\%$ |
| | D Yes | $N_{21} = 81$<br>$r_{21} = r_{FN} = 31\%$ | $N_{22} = 181$<br>$r_{22} = 69\%$ |

$r_{tot} = 155/441 = 35\%$

What is claimed is:

1. A computer-based system for predicting future health of individuals comprising:
   (a) a computer comprising a processor containing a database of longitudinally-acquired biomarker values from individual members of a test population, subpopulation D of said members being identified as having acquired a specified biological condition within a specified time period or age interval and a subpopulation $\overline{D}$ being identified as not having acquired the specified biological condition within the specified time period or age interval; and
   (b) a computer program that includes steps for:
      (1) selecting from said biomarkers a subset of biomarkers for discriminating between members belonging to the subpopulations D and $\overline{D}$, wherein the subset of biomarkers is selected based on distributions of the biomarker values of the individual members of the test population; and
      (2) using the distributions of the selected biomarkers to develop a statistical procedure that is capable of being used for:
         (i) classifying members of the test population as belonging within a subpopulation PD having a prescribed high probability of acquiring the specified biological condition within the specified time period or age interval or as belonging within a subpopulation $\overline{PD}$ having a prescribed low probability of acquiring the specified biological condition within the specified time period or age interval; or
         (ii) estimating quantitatively, for a member of the test population, the probability of acquiring the specified biological condition within the specified time period or age internal;
   wherein changes in said longitudinally-acquired biomarker values are used to develop said statistical procedure.

2. The computer-based system of claim 1 wherein the statistical procedure comprises a discriminant function utilizing estimated mean vectors and estimated covariance matrices of the distributions of biomarker values within the subpopulations D and $\overline{D}$.

3. The computer-based system of claim 2 wherein estimates of parameters of the distributions of the selected biomarkers are obtained by fitting a general linear mixed model to the biomarker data from the test population.

4. The computer-based system of claim 2 wherein:
   (a) the estimated mean vectors are modeled as vector-valued functions of expected-value parameters or values of covariates; or
   (b) the estimated covariance matrices are modeled as matrix-valued functions of covariance parameters or values of covariates.

5. The computer-based system of claim 4 wherein estimates of parameters of the distributions of the selected biomarkers are obtained by fitting a general linear mixed model to the biomarker data from the test population.

6. The computer-based system of claim 4 wherein an estimated mean vector or probability incorporates an estimate of the realized value of a random subject effect vector for a member being classified or of a member for whom a probability is estimated.

7. The computer-based system of claim 6 wherein estimates of parameters of the distributions of the selected biomarkers are obtained by fitting a general linear mixed model to the biomarker data from the test population.

8. A method of predicting an individual's health comprising:
   collecting a plurality of biomarker values from an individual, wherein at least one of said biomarker values is obtained by physically measuring the biomarker value; and
   applying a statistical procedure to said plurality of biomarker values so as:
      (i) to classify said individual as having a prescribed high probability of acquiring a specified biological condition within a specified time period or age interval or as having a prescribed low probability of acquiring the specified biological condition within the specified time period or age interval; or
      (ii) to estimate quantitatively for said individual the probability of acquiring the specified biological condition within the specified time period or age interval;
   wherein said statistical procedure is based on:
      (1) collecting a database of longitudinally-acquired biomarker values from individual members of a test population, subpopulation D of said members being identified as having acquired the specified biological condition within the specified time period or age interval and a subpopulation $\overline{D}$ being identified as not having acquired the specified biological condition within the specified time period or age interval;
      (2) selecting from said biomarkers a subset of biomarkers for discriminating between members belonging to the subpopulations D and $\overline{D}$, wherein the subset of biomarker is selected based on distributions of the biomarker values of the individual members of the test population; and
      (3) using the distributions of the selected biomarkers to develop said statistical procedure;
   wherein changes in said longitudinally-acquired biomarkers values are used to develop said statistical procedure.

9. The method according to claim 8 wherein at least one of said biomarker values is obtained from a biological sample.

10. The method according to claim 9 wherein said biological sample is a serum or urine sample.

11. A computer-based system for predicting an individual's future health comprising:
(a) a computer comprising a processor containing a plurality of biomarker values from an individual; and
(b) a computer program that includes steps for applying a statistical procedure to said plurality of biomarker values so as:
(i) to classify said individual as having a prescribed high probability of acquiring a specified biological condition within a specified time period or age interval or as having a prescribed low probability of acquiring the specified biological condition within the specified time period or age interval; or
(ii) to estimate quantitatively for said individual the probability of acquiring the specified biological condition within the specified time period or age interval;
wherein said statistical procedure is based on:
(1) collecting a database of longitudinally-acquired biomarker values from individual members of a test population, subpopulation D of said members being identified as having acquired the specified biological condition within the specified time period or age interval and a subpopulation $\overline{D}$ being identified as not having acquired the specified biological condition within the specified time period or age interval;
(2) selecting from said biomarkers a subset of biomarkers for discriminating between members belonging to the subpopulations D and $\overline{D}$, wherein the subset of biomarkers is selected based on distributions of the biomarker values of the individual members of the test population; and
(3) using the distributions of the selected biomarkers to develop said statistical procedure;
wherein changes in said longitudinally-acquired biomarker values are used to develop said statistical procedure.

12. The computer-based system of claim 11 wherein the plurality of biomarker values from said individual includes longitudinally-acquired biomarker values.

13. The computer-based system of claim 11 wherein the specified biological condition is death due to a specified underlying cause of death within the specified time period or age interval.

14. The computer-based system of claim 11 wherein the specified biological condition is a specified morbidity within the specified time period or age interval.

15. The computer-based system of claim 11 wherein the specified time period is a period of at least two years.

16. The computer-based system of claim 11 wherein the specified time period is a period of at least three years.

17. A method for assessing an individual's future risk of death from specified underlying causes of death comprising:
collecting a plurality of biomarker values from an individual, wherein at least one of said biomarker values is obtained by physically measuring the biomarker value; and
applying a statistical procedure to said plurality of biomarker values so as to determine whether said individual is classified as having a prescribed high probability of dying, within a specified time period or age interval, from any one of the underlying causes of death that account in the aggregate for at least 60% of all deaths in a test population over the specified time period or age interval.

18. A method for assessing an individual's evidence of good health comprising:
collecting a plurality of biomarker values from an individual, wherein at least one of said biomarker values is obtained by physically measuring the biomarker value; and
applying a statistical procedure to said plurality of biomarker values so as to determine whether said individual is classified as having a prescribed high probability of not dying, within a specified time period or age interval, from any one of the underlying causes of death that account in the aggregate for at least 60% of all deaths in a test population over the specified time period or age interval.

19. A computer-based system for assessing an individual's future risk of death from a specified underlying cause of death comprising:
(a) a computer comprising a processor containing a plurality of biomarker values from an individual; and
(b) a computer program that includes steps for applying a statistical procedure to said plurality of biomarker values so as to determine whether said individual is classified as having a prescribed high probability of dying, within a specified time period or age interval, from any one of the underlying causes of death that account in the aggregate for at least 60% of all deaths in a test population over the specified time period or age interval.

20. A computer-based system for assessing an individual's evidence of good health comprising:
(a) a computer comprising a processor containing a plurality of biomarker values from an individual; and
(b) a computer program that includes steps for applying a statistical procedure to said plurality of biomarker values so as to determine whether said individual is classified as having a prescribed high probability of not dying, within a specified time period or age interval, from any one of the underlying causes of death that account in the aggregate for at least 60% of all deaths in a test population over the specified time period or age interval.

21. An apparatus for assessing an individual's risk of future health problems comprising:
(a) a stooge device for storing a plurality of biomarker values from an individual; and
(b) a processor coupled to the storage device and programmed:
1) to receive from the storage device said plurality of biomarker values; and
2) to apply a statistical procedure to said plurality of biomarker values so as:
(i) to classify said individual as belonging within a subpopulation PD having a prescribed high probability of acquiring a specified biological condition within a specified time period or age interval or as belonging within a subpopulation $\overline{PD}$ having a prescribed low probability of acquiring the specified biological condition within the specified time period or age interval; or
(ii) to estimate quantitatively the probability for said individual acquiring the specified biological condition within the specified time period or age interval;

wherein said statistical procedure is based on:
(1) collecting a database of longitudinally-acquired biomarker values from individual members of a test population, subpopulation D of said members being identified as having acquired the specified biological condition within the specified time period or age interval and a subpopulation $\overline{D}$ being identified as not having acquired the specified biological condition within the specified time period or age interval;
(2) selecting from said biomarkers a subset of biomarkers for discriminating between members belonging to the subpopulations D and $\overline{D}$, wherein the subset of biomarkers is selected based on distributions of the biomarker values of the individual members of the test population; and
(3) using the distributions of the selected biomarkers to develop said statistical procedure;
wherein changes in said longitudinally-acquired biomarker values are used to develop said statistical procedure.

22. A method of predicting an individual's health comprising:
collecting a plurality of biomarker values from an individual, wherein at least one of said biomarker values is obtained by physically measuring the biomarker value; and
applying a multivariate statistical procedure to said plurality of biomarker values so as to provide a statistically-based quantitative probability of said individual acquiring a specified morbidity or suffering a mortality with a specified underlying cause of death within a specified time period or age interval, wherein said multivariate statistical procedure is based on comparing said individual's plurality of biomarker values with a longitudinally-acquired database, wherein said database includes biomarker values from individual members of a test population, a subpopulation D of said members being identified as having acquired the specified morbidity or suffering the mortality with the specified underlying cause of death within the specified time period or age interval and a subpopulation D being identified as not having acquired the specified morbidity or suffering the mortality with the specified underlying cause of death within the specified time period or age interval;
wherein changes in the longitudinally-acquired biomarker values to develop said statistical procedure.

23. The method according to claim 22 wherein said method includes the step of selecting a subset of biomarkers having discriminatory power for discriminating between said members identified as having acquired the specified biological condition within the specified time period or age interval and said members identified as not having acquired the specified biological condition within the specified time period or age interval.

24. The method according to claim 23 wherein the biomarkers in said subset provide a statistically significant contribution to the discriminatory power of said subset of biomarkers when used in combination with the other biomarkers in said subset.

25. The method according to claim 24 wherein said statistically significant contribution to the discriminatory power is established based on selecting the biomarkers in said subset by evaluating distributions of said longitudinally-acquired biomarker values.

26. The method according to claim 24 wherein said statistically significant contribution to the discriminatory power is established based on evaluating ratios or longitudinally-observed changes in the ratios of an individual's biomarker values.

27. The method according to claim 26 wherein the evaluation step comprises assessing whether longitudinal trends in said longitudinally-acquired biomarkers values are statistically correlated with acquisition of the specified biological condition.

28. The method according to claim 22 wherein said database comprises longitudinally-acquired biomarker values and at least one of said longitudinally-acquired biomarker values is obtained by physically measuring the biomarker value.

29. A computer-based system for predicting the future health of individuals comprising:
(a) a computer comprising a processor containing:
(i) a plurality of biomarker values from an individual; and
(ii) a longitudinally-acquired database, wherein said database includes biomarker values from individual members of a test population, subpopulation D of said members being identified as having acquired a specified morbidity or suffering a mortality with a specified underlying cause of death within a specified time period or age interval and a subpopulation $\overline{D}$ being identified as not having acquired the specified morbidity or suffering a mortality with the specified underlying cause of death within the specified time period or age interval; and
(b) a computer program that includes steps for applying a multivariate statistical procedure to compare said individual's plurality of biomarker values with said longitudinally-acquired database so as to provide a statistically-based quantitative probability for said individual acquiring the specified morbidity or suffering a mortality with the specified underlying cause of death within the specified time period or age interval;
wherein changes in the longitudinally-acquired biomarker values are used to develop said statistical procedure.

30. An apparatus for assessing an individuals's an risk off future health problems comprising:
(a) a storage device for storing a plurality of biomarker values from an individual; and
(b) a processor coupled to said storage device, said processor being programmed to receive from said storage device said plurality of biomarker values and apply a multivariate statistical procedure comparing said plurality of biomarker values with a longitudinally-acquired database, wherein said database includes biomarker values from individual members of a test population, subpopulation D of said members being identified as having acquired a specified morbidity or suffering a mortality with a specified underlying cause of death within a specified time period or age interval, and a subpopulation $\overline{D}$ being identified as not having acquired the specified morbidity or suffering a mortality with the specified underlying cause of death within the specified time period or age interval, so as to provide a statistically-based quantitative probability for said individual acquiring the specified morbidity or suffering a mortality with the specified underlying cause of death within the specified time period or age interval;
wherein changes in the longitudinally-acquired biomarker values are used to develop said statistical procedure.

* * * * *

UNITED STATES PATENT AND TRADEMARK OFFICE
CERTIFICATE OF CORRECTION

PATENT NO. : 6,059,724
DATED : May 9, 2000
INVENTOR(S) : Campbell et al.

It is certified that error appears in the above-identified patent and that said Letters Patent is hereby corrected as shown below:

Title page,
Item [75], Inventors, "T. Colin Campell" should be changed to -- T. Colin Campbell --;
Item [73], Assignee, "BioSignal" should be changed to -- BioSignia --;
Item [57], ABSTRACT,
Line 6, "D of aid members being" should be changed to -- D of said members being --;

Column 2,
Line 19, "A living, person" should be changed to -- A living person --.

Column 6,
Line 67, "that may included in the" should be changed to -- that may be included in the, --;

Column 19,
Lines 50 and 51, "A representative embodiment...are" should be changed to
-- A representative embodiment...is --;

Column 20,
Line 42, "subjects whose age falls" should be changed to -- subjects whose ages fall --.
Line 60, "to compile list all" should be changed to -- to compile a list of all --.

Column 24,
Line 2, "vector Y of (resealed)" should be changed to -- vector Y of (rescaled) --.

Column 29,
Line 61, "$d_i = \Delta_i Z_i \Sigma_i^{-1}$" (grouped with prior definition) should be changed to -- (place on separate line as in supplied text) --;

Column 30,
Line 12, "upon the estimated values, $\hat{Y}_i$." should be changed to -- upon the estimated values, $\hat{Y}_i$: --;
Line 17, "group 2 (Group PD)" should be changed to -- group 2 (Group PD) --;
Line 25, "values, $Y_i$ (min)." should be changed to -- values, $Y_i$ (min): --.

Column 31,
Line 37, "probability that a newt subject" should be changed to -- probability that a new subject --.

Column 33,
Line 32, ""knower important" biomarker" should be changed to -- "known important" biomarker --.

UNITED STATES PATENT AND TRADEMARK OFFICE
CERTIFICATE OF CORRECTION

PATENT NO. : 6,059,724
DATED : May 9, 2000
INVENTOR(S) : Campbell et al.

It is certified that error appears in the above-identified patent and that said Letters Patent is hereby corrected as shown below:

Column 34,
Line 34, "different than time trend" should be changed to -- different than the time trend --;
Line 60, "specifications listed below, obtain" should be changed to -- specifications listed below; obtain, --;

Column 36,
Line 39, "and 79 (448%) were" should be changed to -- and 79 (44%) were --;

Column 37,
Line 47, "procedures effectively classifies" should be changed to -- procedures effectively classify --.

Column 47,
Line 64, "period or age internal" should be changed to -- period or age interval; --.

Column 50,
Line 48, "a) a stooge device for" should be changed to -- a) a storage device for --.

Column 51,
Line 41, "and a subpopulation D" should be changed to -- and a subpopulation $\bar{D}$ --;
Line 47, "values to develop said" should be changed to -- values are used to develop said --;

Column 52,
Line 6, "in said...biomarkers values" should be changed to -- in said... biomarkers' values --;

Signed and Sealed this

Nineteenth Day of July, 2005

JON W. DUDAS
*Director of the United States Patent and Trademark Office*